US012605435B2

(12) United States Patent
An et al.

(10) Patent No.: US 12,605,435 B2
(45) Date of Patent: Apr. 21, 2026

(54) MULTIVALENT PNEUMOCOCCAL POLYSACCHARIDE-PROTEIN CONJUGATE COMPOSITION

(71) Applicants: SANOFI PASTEUR INC., Swiftwater, PA (US); SK BIOSCIENCE CO., LTD., Seongnam-si (KR)

(72) Inventors: Kyungjun An, Seoul (KR); Dongsoo Ham, Suwon-si (KR); Hun Kim, Suwon-si (KR); Sunghyun Kim, Yongin-si (KR); Jinhwan Shin, Seoul (KR); Robert Hopfer, Roaring Brook Township, PA (US); Richard D. Kensinger, Henryville, PA (US); Moe Kyaw, Swiftwater, PA (US); Philippe Talaga, Lyons Cedex (FR)

(73) Assignees: SANOFI PASTEUR INC., Swiftwater, PA (US); SK BIOSCIENCE CO., LTD., Seoul (KR)

( * ) Notice: Subject to any disclaimer, the term of this patent is extended or adjusted under 35 U.S.C. 154(b) by 0 days.

(21) Appl. No.: 18/419,900

(22) Filed: Jan. 23, 2024

(65) Prior Publication Data

US 2024/0238399 A1 Jul. 18, 2024

Related U.S. Application Data

(63) Continuation of application No. 17/471,825, filed on Sep. 10, 2021, now Pat. No. 11,911,452, which is a continuation of application No. 16/966,584, filed as application No. PCT/US2019/016511 on Feb. 4, 2019, now Pat. No. 11,123,417.

(60) Provisional application No. 62/626,509, filed on Feb. 5, 2018.

(30) Foreign Application Priority Data

Apr. 18, 2018 (KR) ........................ 10-2018-0045246

(51) Int. Cl.
| A61K 39/09 | (2006.01) |
| A61K 9/00 | (2006.01) |
| A61K 39/00 | (2006.01) |

(52) U.S. Cl.
CPC .......... *A61K 39/092* (2013.01); *A61K 9/0019* (2013.01); *A61K 2039/6031* (2013.01); *A61K 2039/70* (2013.01)

(58) Field of Classification Search
CPC ................................................. A61K 39/092
See application file for complete search history.

(56) References Cited

U.S. PATENT DOCUMENTS

| 5,153,312 A | 10/1992 | Porro |
| 5,773,007 A | 6/1998 | Penney et al. |
| 6,132,723 A | 10/2000 | Malcolm |
| 6,168,796 B1 | 1/2001 | Malcolm |
| 7,709,001 B2 | 5/2010 | Hausdorff et al. |
| 7,862,823 B1 | 1/2011 | Leroy |
| 7,955,605 B2 | 6/2011 | Prasad |
| 11,123,417 B2 | 9/2021 | An et al. |
| 11,147,864 B2 | 10/2021 | An et al. |
| 11,224,652 B2 | 1/2022 | An et al. |
| 11,241,489 B2 | 2/2022 | An et al. |
| 11,911,452 B2 * | 2/2024 | An ........................ A61K 39/092 |
| 12,440,548 B2 | 10/2025 | Kim et al. |
| 2003/0099672 A1 | 5/2003 | Schultz |
| 2005/0009121 A1 | 1/2005 | Talaga et al. |
| 2011/0117123 A1 | 5/2011 | Leroy |
| 2011/0195086 A1 | 8/2011 | Caulfield et al. |
| 2011/0212124 A1 | 9/2011 | Boutriau et al. |
| 2012/0052088 A1 | 3/2012 | Davis et al. |

(Continued)

FOREIGN PATENT DOCUMENTS

| AU | 2007200116 A1 | 1/2007 |
| AU | 2010235979 A1 | 11/2010 |

(Continued)

OTHER PUBLICATIONS

Bethell et al., "A Novel Method of Activation of Cross-linked Agaroses with 1, 1'-Carbonyldiimidazole Which Gives a Matrix for Affinity Chromatography Devoid of Additional Charged Groups", The Journal of Biological Chemistry, 1979, vol. 245, No. 8, pp. 2572-2574.
Extended European Search Report dated Mar. 18, 2022 for corresponding European Patent Application No. 19748037.9, 12 pages.
Extended European Search Report dated Mar. 18, 2022 for European Patent Application No. 19747393.7, 12 pages.
Anderson et al., "Non-interference between two protein carriers when used with the same polysaccharide for pneumococcal conjugate vaccines in 2-year-old children," Vaccine, 2003, vol. 21, No. 13-14, pp. 1554-1559.

(Continued)

*Primary Examiner* — Albert M Navarro
(74) *Attorney, Agent, or Firm* — MH2 Technology Law Group, LLP

(57) ABSTRACT

Provided are mixed carrier, multivalent pneumococcal conjugate compositions comprising 21 different pneumococcal capsular polysaccharide-protein conjugates, wherein each of the conjugates includes a capsular polysaccharide from a different serotype of *Streptococcus pneumoniae* conjugated to either tetanus toxoid (TT) or $CRM_{197}$, wherein the *Streptococcus pneumoniae* serotypes are selected from 1, 3, 4, 5, 6A, 6B, 7F, 8, 9N, 9V, 10A, 11A, 12F, 14, 15B, 18C, 19A, 19F, 22F, 23F, and 33F, where the capsular polysaccharides of two of serotypes 1, 3, and 5 and one or both of serotypes 15B and 22F are conjugated to TT and the remaining capsular polysaccharides are conjugated to $CRM_{197}$. Also provided are methods of producing the mixed carrier, multivalent pneumococcal conjugate compositions and methods of using the same for prophylaxis against *Streptococcus pneumoniae* infection or disease in a subject.

15 Claims, No Drawings

(56) References Cited

U.S. PATENT DOCUMENTS

| | | |
|---|---|---|
| 2012/0328659 A1 | 12/2012 | Denoel et al. |
| 2013/0072881 A1 | 3/2013 | Khandke et al. |
| 2013/0266609 A1 | 10/2013 | Boutriau |
| 2014/0099337 A1 | 4/2014 | Davis et al. |
| 2014/0322263 A1 | 10/2014 | Siber et al. |
| 2015/0190520 A1 | 7/2015 | Shin et al. |
| 2015/0202309 A1 | 7/2015 | Emini et al. |
| 2015/0265702 A1 | 9/2015 | Biemans et al. |
| 2015/0343076 A1 | 12/2015 | Park et al. |
| 2016/0375118 A1 | 12/2016 | Park et al. |
| 2017/0157241 A1 | 6/2017 | Li |
| 2018/0000922 A1 | 1/2018 | Cooper et al. |
| 2019/0192648 A1 | 6/2019 | Smith et al. |
| 2020/0230233 A1 | 7/2020 | An et al. |
| 2020/0237889 A1 | 7/2020 | An et al. |
| 2020/0360502 A1 | 11/2020 | An et al. |
| 2021/0077608 A1 | 3/2021 | An et al. |
| 2021/0154287 A1 | 5/2021 | Kim et al. |
| 2021/0283247 A1 | 9/2021 | Hausdorff et al. |
| 2021/0401963 A1 | 12/2021 | An et al. |
| 2022/0031828 A1 | 2/2022 | An et al. |
| 2022/0265803 A1 | 8/2022 | An et al. |
| 2024/0207384 A1 | 6/2024 | Kim et al. |

FOREIGN PATENT DOCUMENTS

| | | | |
|---|---|---|---|
| CA | 2153730 A1 | 1/1997 | |
| CA | 2153733 A1 | 1/1997 | |
| CN | 1060408 A | 4/1992 | |
| CN | 1255861 A | 6/2000 | |
| CN | 101180079 A | 5/2008 | |
| CN | 101785857 A | 7/2010 | |
| CN | 101818185 A | 9/2010 | |
| CN | 102068690 A | 5/2011 | |
| CN | 102858365 A | 1/2013 | |
| CN | 103599529 A | 2/2014 | |
| CN | 103623401 A | 3/2014 | |
| CN | 103656631 A | 3/2014 | |
| CN | 103656632 A | 3/2014 | |
| CN | 107029225 A | 8/2017 | |
| EP | 0497524 B1 | 5/1992 | |
| EP | 2932979 A1 | 10/2015 | |
| IN | 201917040656 | 8/2019 | |
| KR | 10-2018-0027353 A | 3/2018 | |
| TW | 201008577 A | 3/2010 | |
| TW | I341210 B | 5/2011 | |
| WO | 96/40225 A1 | 12/1996 | |
| WO | 9851339 A1 | 11/1998 | |
| WO | 00/56359 A2 | 9/2000 | |
| WO | 02/00249 A2 | 1/2002 | |
| WO | 02/080965 A2 | 10/2002 | |
| WO | 03/051392 A2 | 6/2003 | |
| WO | 2006/032499 A1 | 3/2006 | |
| WO | 2009/000824 A2 | 12/2008 | |
| WO | 2009/000826 A1 | 12/2008 | |
| WO | 2009000825 A2 | 12/2008 | |
| WO | 2010/125480 A1 | 11/2010 | |
| WO | 2011/100151 A1 | 8/2011 | |
| WO | 2013/191459 A1 | 12/2013 | |
| WO | 2014/027302 A1 | 2/2014 | |
| WO | 2014/092377 A1 | 6/2014 | |
| WO | 2014/118201 A1 | 8/2014 | |
| WO | 2015/110940 A2 | 7/2015 | |
| WO | 2015/110941 A2 | 7/2015 | |
| WO | 2015/110942 A2 | 7/2015 | |
| WO | 2016/207905 A2 | 12/2016 | |
| WO | 2017/067962 A1 | 4/2017 | |
| WO | 2017/085586 A1 | 5/2017 | |
| WO | 2017/173415 A2 | 10/2017 | |
| WO | 2018/027123 A1 | 2/2018 | |
| WO | 2018/027126 A1 | 2/2018 | |
| WO | 2018/06444 A1 | 4/2018 | |
| WO | 2018/064444 A1 | 4/2018 | |
| WO | 2019/050813 A1 | 3/2019 | |
| WO | 2019/050815 A1 | 3/2019 | |
| WO | 2019/050816 A1 | 3/2019 | |
| WO | 2019/050818 A1 | 3/2019 | |
| WO | 2019/070994 A1 | 4/2019 | |
| WO | 2019/152921 A1 | 8/2019 | |
| WO | 2019/152925 A1 | 8/2019 | |
| WO | 2021/021729 A1 | 2/2021 | |

OTHER PUBLICATIONS

Sigurdardottir et al., "Immune response to octavalent diphtheria- and tetanus-conjugated pneumococcal vaccines is serotype- and carrier-specific: the choice for a mixed carrier vaccine," The Pediatric Infectious Disease Journal, 2002, vol. 21, No. 6, pp. 548-554.

Wuorimaa et al., "Tolerability and immunogenicity of an eleven-valent pneumococcal conjugate vaccine in healthy toddlers," The Pediatric Infectious Disease Journal, 2001, vol. 20, No. 3, pp. 272-277.

Extended European Search Report dated Mar. 16, 2022 for European Patent Application No. 19788873.8, 14 pages.

International Search Report dated Jul. 16, 2019 for International Application No. PCT/KR2019/004717, 20 pages with English translation.

Google Translation of WO-2013/191459-A1 dated Dec. 27, 2013, entitled "Polyvalent Pneumococcal Polysaccharide-Protein Conjugate Composition".

Office Action dated Aug. 1, 2022 for U.S. Appl. No. 17/047,563, 38 pages.

Dagan et al., "Reduction of Antibody Response to an 11-Valent Pneumococcal Vaccine Coadministered with a Vaccine Containing Acellular Pertussis Components", Infection and Immunity, Sep. 2004, vol. 72, No. 9, pp. 5383-5391.

N. Renggli-Zulliger (Authorized Officer), International Search Report and Written Opinion dated Nov. 4, 2020 for International Application No. PCT/US2020/043729, 12 pages.

Final Office Action dated Mar. 1, 2023 for U.S. Appl. No. 17/047,563, 20 pages.

Final Office Action for U.S. Appl. No. 17/500,716 dated Dec. 16, 2024, 16 pages.

Office Action for U.S. Appl. No. 17/630,841 dated Dec. 6, 2024, 18 pages.

Office Action for U.S. Appl. No. 18/598,439 dated Dec. 13, 2024, 10 pages.

Written Opinion and Search Report dated Sep. 6, 2024 for Taiwan Patent Application No. 112144714, 12 pages including (Machine) English translation.

International Search Report and Written Opinion dated Oct. 24, 2017 from International Application No. PCT/US2017/045483 (Authorized Officer, Blaine R. Copenheaver), 10 Pages.

Durando et al., "Experience with pneumococcal polysaccharide conjugate vaccine (conjugated to CRM197 carrier protein) in children and adults", Clinical Microbiology Infection, Oct. 1, 2013, vol. 19, Suppl. 1, pp. 1-9.

Daniels et al., "A Review of Pneumococcal Vaccines: Current Polysaccharide Vaccine Recommendations and Future Protein Antigens", J Pediatr Pharmacol Ther, 2016, vol. 21, No. 1, pp. 27-35.

International Search Report and Written Opinion dated Oct. 30, 2017 from International Application No. PCT/US2017/045479 (Authorized Officer, Shane Thomas), 9 Pages.

Jakobsen et al., "Intranasal Immunization with Pneumococcal Polysaccharide Conjugate Vaccines Protects Mice against Invasive Pneumococcal Infections", Infection and Immunity, Aug. 1999, vol. 67, No. 8, pp. 4128-4133.

Prymula et al., "Pneumococcal capsular polysaccharides conjugated to protein D for prevention of acute otitis media caused by both Streptococcus pneumoniae and non-typable Haemophilus influenzae: a randomised double-blind efficacy study", Lancet, 2006, vol. 367, pp. 740-748.

Fattom et al., "Serum Antibody Response in Adult Volunteers Elicited by Injection of Streptococcus pneumoniae Type 12F Polysaccharide Alone or Conjugated to Diphtheria Toxoid", Infection and Immunity, Jul. 1990, vol. 58, No. 7, pp. 2309-2312.

(56) References Cited

OTHER PUBLICATIONS

Andrews et al., "Serotype-specific effectiveness and correlates of protection for the 13-valent pneumococcal conjugate vaccine: a postlicensure indirect cohort study", Lancet Infect. Dis., Jul. 18, 2014, 8 pages.

Juergens et al., "Post Hoc Analysis of a Randomized Double-Blind Trial of the Correlation of Functional and Binding Antibody Responses Elicited by 13-Valent and 7-Valent Pneumococcal Conjugate Vaccines and Association with Nasopharyngeal Colonization", Clinical and Vaccine Immunology, Sep. 2014, vol. 21, No. 9, pp. 1277-1281.

Nurkka et al., "Serum and salivary anti-capsular antibodies in infants and children vaccinated with octavalent pneumococcal conjugate vaccines, PncD and PncT", Vaccine, 2002, vol. 20, pp. 194-201.

Pfizer, "PREVNAR 13 (Pneumococcal 13-valent Conjugate Vaccine [Diphtheria CRM197 Protein]) Suspension for intramuscular injection", Prevnar 13 Full Prescribing Information, 2010, 47 pages.

Vesikari et al., "Immunogenicity of the 10-Valent Pneumococcal Non-typeable Haemophilus influenzae Protein D Conjugate Vaccine (PHiD-CV) Compared to the Licensed 7vCRM Vaccine", The Pediatric Infectious Disease Journal, Apr. 2009, vol. 28, No. 4, Supplement pages S66-S76.

Wuorimaa et al., "Tolerability and immunogenicity of an 11-valent pneumococcal conjugate vaccine in adults", Vaccine, 2001, vol. 19, pp. 1863-1869.

International Search Report and Written Opinion dated Apr. 15, 2019 from International Application No. PCT/US2019/016506 (Authorized Officer, Shane Thomas), 11 Pages.

Extended European Search Report dated Mar. 10, 2020 for European Patent Application No. 17837752.9, 12 pages.

Dagan et al., "Tolerability and immunogenicity of an eleven valent mixed carrier *Streptococcus pneumoniae* capsular polysaccharide-diphtheria toxoid or tetanus protein conjugate vaccine in Finnish and Israeli infants", The Pediatric Infectious Disease Journal, Feb. 2004, vol. 23, No. 2, pp. 91-98.

International Search Report and Written Opinion dated Jul. 1, 2019 from International Application No. PCT/US2019/016511 (Authorized Officer, Lee W. Young), 9 pages.

Martens et al., "Serotype-specific mortality from invasive *Streptococcus pneumoniae* disease revisited", BMC Infectious Diseases, 2004, vol. 4, No. 21, 7 pages.

Sanofi's Opposition to Pfizer's Motion to Amend dated Nov. 16, 2018 from IPR Trial No. IPR2018-00187 for U.S. Pat. No. 9,492,559 (*Sanofi Pasteur Inc. and SK Chemicals Co., Ltd.* vs. *Pfizer, Inc.*), 42 pages.

Loek Van Alphen, "Exhibit 1101, Declaration of Loek Van Alphen, PH.D. in Support of Sanofi's Opposition to Motion to Amend" dated Nov. 14, 2018 from IPR Trial No. IPR2018-00187 for U.S. Pat. No. 9,492,559 (*Sanofi Pasteur Inc. and SK Chemicals Co., Ltd.* vs. *Pfizer, Inc.*), 78 pages.

Loek Van Alphen, "Exhibit 2073, Deposition of Loek Van Alphen, PH.D." dated Dec. 10, 2018 from IPR Trial No. IPR2018-00187 for U.S. Pat. No. 9,492,559 (*Sanofi Pasteur Inc. and SK Chemicals Co., Ltd.* vs. *Pfizer, Inc.*), 201 pages.

Peter R. Paradiso, "Exhibit 1116, Deposition of Peter R. Paradiso, PH.D." dated Jan. 10, 2019 from IPR Trial No. IPR2018-00187 for U.S. Pat. No. 9,492,559 (*Sanofi Pasteur Inc. and SK Chemicals Co., Ltd.* vs. *Pfizer, Inc.*), 125 pages.

Peter R. Paradiso, "Exhibit 2074, Declaration of Peter R. Paradiso, PH.D in Support of Pfizer's Reply in Support of Motion to Amend" dated Dec. 18, 2018 from IPR Trial No. IPR2018-00187 for U.S. Pat. No. 9,492,559 (*Sanofi Pasteur Inc. and SK Chemicals Co., Ltd.* vs. *Pfizer, Inc.*), 23 pages.

Chen et al., "Safety and immunogenicity of a new 13-valent pneumococcal conjugate vaccine versus a licensed 7-valent pneumococcal conjugate vaccine: a study protocol of a randomised non-inferiority trial in China", BMJ Open, Oct. 19, 2016, e012488, 9 pages.

International Search Report and Written Opinion dated Apr. 11, 2020 from International Application No. PCT/US2020/043729, (Authorized Officer, N. Renggli-Zulliger), 12 pages.

Beall et al., "A Population-Based Descriptive Atlas of Invasive Pneumococcal Strains Recovered Within the U.S. During 2015-2016", Frontiers in Microbiology, Nov. 19, 2018, vol. 9, 19 pages.

Van der Linden et al., "Increase of serotypes 15A and 23B in IPD in Germany in the PCV13 vaccination era", BMC Infectious Diseases, May 5, 2015, vol. 15, No. 1, p. 207, 12 pages.

Yano et al., "Characterization of Gene Use and Efficacy of Mouse Monoclonal Antibodies to *Streptococcus pneumoniae* Serotype 8", Clinical and Vaccine Immunology, 2011, vol. 18, No. 1, pp. 59-66.

Buchwald et al., "A Peptide Mimotope of Type 8 Pneumococca Capsular Polysaccharide Induces a Protective Immune Response in Mice", Infection and Immunity, 2005, vol. 73, No. 1, pp. 325-333.

Malcolm et al., "Chapter 21: Surface Layers from Bacillus alvei as a Carrier for a *Streptococcus pneumoniae* Conjugate Vaccine", In: Beveridge T.J., Koval S.F. (eds.), Advances in Bacterial Paracrystalline Surface Layers. Nato ASI Series (Series A: Life Sciences), 1993, vol. 252, pp. 219-233.

Malcolm et al., "Chapter 13: Crystalline Bacterial Cell Surface Layers (S-Layers) as Combined Carrier/Adjuvants for Conjugate Vaccines", In: Sleytr U.B., Messner P., Pum D., Sára M. (eds.), Immobilised Macromolecules: Application Potentials. Springer Series in Applied Biology. Springer, London, 1993, pp. 195-207.

Malcolm et al., "S30: Improved Immunogenicity Using Oligosaccharide Conjugate Vaccines", Glyco XIII: XIIIth International Symposium on Glycoconjugates; Seattle, USA, Aug. 20-26, 1995, Glycoconjugate Journal, 1995, vol. 12, p. 560.

Jahn-Schmid et al., "Toward selective elicitation of TH1-controlled vaccination responses: vaccine applications of bacterial surface layer proteins", Journal of Biotechnology, 1996, vol. 44, pp. 225-231.

Thanos et al., "Invasive Infektion durch Streptococcus pneumoniae Serotyp 8 im Säuglingsalter", Monatsschr Kinderheilkd, 2013, vol. 161, pp. 1177-1179, with English abstract.

Office Action dated Aug. 10, 2020 for U.S. Appl. No. 16/322,698, 23 pages.

Office Action dated Mar. 25, 2021 for U.S. Appl. No. 16/322,698, 13 pages.

Office Action dated Mar. 15, 2021 for U.S. Appl. No. 16/322,726, 21 pages.

Boot et al., "Simultaneous vaccination with Prevenar and multicomponent vaccines for children: Interference or no interference?", Human Vaccines, 2009, vol. 5, No. 1, pp. 15-17.

Kolberg et al., "Monoclonal antibodies with specifities for Streptococcus pneumoniae group 9 capsular polysaccharides", FEMS Immunology and Medical Microbiology, 1998, vol. 20, pp. 249-255.

Non-Final Office Action dated Jul. 16, 2024 for U.S. Appl. No. 17/500,716, 5 pages.

Nuriev et al., "Immunochemical and Protective Properties of Conjugated Capsular Polysaccharide of *Streptococcus pneumoniae* Serotype 9N", Applied Biochemistry and Microbiology, 2018, vol. 54, No. 9, pp. 869-875.

Office Action dated Jul. 9, 2024 for Japanese Patent Application No. 2023-117178, 6 pages with English translation.

Kovtun et al., "Next Generation Pneumococcal Conjugate Vaccines Efficacy in Different Regions of the World", Current Pediatrics, 2014, vol. 13, No. 1, pp. 18-25 with English Abstract.

Non-Final Office Action dated Jul. 5, 2023 for U.S. Appl. No. 17/047,563, 10 pages.

Notice of Allowance and Examiner-Initiated Interview Summary dated May 12, 2021 for U.S. Appl. No. 16/966,552, 20 pages.

Notice of Allowance dated Sep. 7, 2021 for U.S. Appl. No. 16/322,726, 13 pages.

Notice of Allowance dated Oct. 29, 2021 for U.S. Appl. No. 16/322,726, 18 pages.

Notice of Allowance dated Sep. 14, 2021 for U.S. Appl. No. 16/966,552, 14 pages .

Notice of Allowance and Applicant-Initiated Interview Summary dated Sep. 23, 2021 for U.S. Appl. No. 16/322,698, 8 pages.

(56) References Cited

OTHER PUBLICATIONS

Notice of Allowance dated Oct. 20, 2021 for U.S. Appl. No. 16/322,698, 14 pages.

Notice of Allowance and Examiner-Initiated Interview Summary dated Dec. 8, 2023 for U.S. Appl. No. 17/047,563, 9 pages.

Fredman, Jeffrey N., et al. (Administrative Patent Judges for U.S. Patent and Trademark Office, Patent Trial and Appeal Board, "Judgment—Final Written Decision on Remand Denying Patent Owner's Motion to Amend as to Proposed Substitute Claims 48 and 49 for Case IPR2018-00187, U.S. Pat. No. 9,492,559 B2, Case IPR2017-02131, U.S. Pat. No. 9,492,559 B2, and Case IPR2017-02132, U.S. Pat. No. 9,492,559 B2," *Sanofi Pasteur Inc et al.* (Petitioners) v. *Pfizer Inc.* (Patent Owner), Filed: Jun. 10, 2024 (Paper No. 84), 35 pages.

Gutman, Siegmund Y., et al. (Counsel for Appellees Sanofi Pasteur Inc. et al.), "Appellees Sanofi Pasteur Inc., and SK Chemicals Co., Ltd's Responsive Brief," *Pfizer Inc.* (Appellant) v. *Sanofi Pasteur Inc et al.* (Appellees), U.S. Court of Appeals for the Federal Circuit, Docket Nos. 2024-2199, 2024-2201, 2024-2202, Filed: May 2, 2025 (Document 31), 75 pages.

Chinese Search Report for Chinese Application No. 202080061473.6 dated Apr. 28, 2025, 4 pages including English translation.

Lourie et al. (Circuit Judges for U.S. Court of Appeals for the Federal Circuit), "Decision on Appeals from the United States Patent and Trademark Office, Patent Trial and Appeal Board in Nos. IPR2017-02131, IPR2017-02132, IPR2017-02136, IPR2017-02138, and IPR2018-00187," *Pfizer Inc.* (Appellant) v. *Sanofi Pasteur Inc. et al.* (Appellees), Appeal Nos. 2019-1871, 2019-1873, 2019-1875, 2019-1876, 2019-2224, Decided: Mar. 5, 2024 (Document 146), 20 pages.

Notice of Allowance and Fee(s) Due for U.S. Appl. No. 18/598,439 dated Apr. 10, 2025, 12 pages.

Notice of Allowance and Fee(s) Due for U.S. Appl. No. 18/598,439 dated Jul. 14, 2025, 43 pages.

Office Action for U.S. Appl. No. 17/630,841 dated Jun. 18, 2025, 36 pages.

Preliminary Office Action and Search Report dated Nov. 7, 2025 for Brazilian Patent Application No. BR112020014978-0, 5 pages including partial informal English translation.

Office Action for U.S. Appl. No. 17/630,841 dated Nov. 6, 2025, 23 pages.

* cited by examiner

MULTIVALENT PNEUMOCOCCAL POLYSACCHARIDE-PROTEIN CONJUGATE COMPOSITION

CROSS REFERENCE TO RELATED APPLICATIONS

This application is a Continuation of U.S. application Ser. No. 17/471,825 filed 10 Sep. 2021 (allowed), which is a Continuation of U.S. application Ser. No. 16/966,584 filed 31 Jul. 2020, issued as U.S. Pat. No. 11,123,417 on 21 Sep. 2021, which is a U.S. National Stage application of PCT/US2019/016511 filed 4 Feb. 2019, which claims the benefit of, and relies on the filing date of, U.S. provisional patent application No. 62/626,509, filed 5 Feb. 2018 and Korean patent application number 10-2018-0045246 filed 18 Apr. 2018, the entire disclosures of which are herein incorporated by reference.

TECHNICAL FIELD

This application relates generally to mixed carrier, multivalent pneumococcal conjugate compositions, vaccines comprising the same and methods of using these compositions and vaccines for prophylaxis of *Streptococcus pneumoniae* infection or disease in a subject.

BACKGROUND

Pneumococcus (*Streptococcus pneumoniae*) is a Gram-positive, lancet-shaped, facultative anaerobic bacteria with over 90 known serotypes. Most *S. pneumoniae* serotypes have been shown to cause disease, with the 23 most common serotypes accounting for approximately 90% of invasive disease worldwide. Serotypes are classified based on the serological response of the capsular polysaccharides, the most important virulence factor for pneumococcus. Capsular polysaccharides are T-cell independent antigens that induce antibody production in the absence of T helper cells. T-cell independent antigens generally induce antibodies with low affinity and short-lived immune responses with little to no immunological memory.

Initial pneumococcal vaccines included combinations of capsular polysaccharides from different serotypes. These vaccines can confer immunity against *S. pneumoniae* in patients with developed or healthy immune systems, however, they were not effective in infants, who lack a developed immune system, and elderly subjects, who often have impaired immune function. To improve the immune response to pneumococcal vaccines, particularly in infants and elderly subjects, who are at higher risk to develop *S. pneumoniae* infection, capsular polysaccharides were conjugated to suitable carrier proteins to create pneumococcal conjugate vaccines. Conjugation to a suitable carrier protein changes the capsular polysaccharide from a T-cell independent antigen to a T-cell dependent antigen. As such, the immune response against the conjugated capsular polysaccharide involves T helper cells, which help induce a more potent and rapid immune response upon re-exposure to the capsular polysaccharide.

There are at least two approaches to developing pneumococcal conjugate vaccines: the single carrier approach and the mixed carrier approach. The immunogenicity of different capsular polysaccharide conjugates may vary depending on the pneumococcal serotype and carrier protein used. In the single carrier approach, the capsular polysaccharides from different serotypes are conjugated to a single protein carrier.

Pfizer's PREVNAR series of vaccines is an example of a single carrier approach where the different capsular polysaccharides are conjugated to the $CRM_{197}$ protein carrier, a non-toxic variant of the diphtheria toxoid having a single amino acid substitution of glutamic acid for glycine. The 7-valent PREVNAR vaccine (PREVNAR) was first approved in 2000 and contains the capsular polysaccharides from the seven most prevalent serotypes: 4, 6B, 9V, 14, 18C, 19F and 23F. The 13-valent vaccine, PREVNAR 13, added the serotypes 1, 5, 7F, 3, 6A, and 19A to the $CRM_{197}$ protein carrier. The protein carrier, $CRM_{197}$, the single carrier used in PREVNAR vaccines has never been used as part of a mixed carrier system in a pneumococcal conjugate vaccine.

The second pneumococcal vaccine approach is the mixed carrier approach. In the mixed carrier approach, instead of using a single protein carrier, two or more protein carriers are used, with capsular polysaccharides from specific serotypes conjugated to a first protein carrier and capsular polysaccharides from different serotypes conjugated to at least a second, different protein carrier. For example, GlaxoSmithKline has developed SYNFLORIX, a 10-valent (serotypes 1, 4, 5, 6B, 7F, 9V, 14, 18C, 19F and 23F), mixed carrier, pneumococcal conjugate vaccine that uses *H influenzae* protein D, tetanus toxoid, and diphtheria toxoid as the protein carriers. In SYNFLORIX, serotypes 1, 4, 5, 6B, 7F, 9V, 14, and 23F are conjugated to protein D; serotype 18C is conjugated to tetanus toxoid; and serotype 19F is conjugated to diphtheria toxoid [2]. Serotype 3 was removed from the 11-valent precursor to SYNFLORIX, in part, because it did not show serotype-specific efficacy in an acute otitis media trial [1]. Another group, Aventis Pasteur, developed an 11-valent (serotypes 1, 3, 4, 5, 6B, 7F, 9V, 14, 18C, 19F, and 23F), mixed carrier, pneumococcal conjugate vaccine using diphtheria toxoid and tetanus toxoid as protein carriers [3]. Capsular polysaccharides from serotypes 3, 9V, 14, and 18C can evoke a better response when conjugated to diphtheria toxoid than they do when conjugated to tetanus toxoid [6]. Thus, serotypes 3, 6B, 14, and 18C were conjugated to diphtheria toxin and serotypes 1, 4, 5, 7F, 9V, 19F, and 23F were conjugated to tetanus toxoid. The development of this mixed carrier, pneumococcal vaccine was terminated due, in part, to technical reasons and the potential of a reduced response when administered with acellular pertussis vaccines [3]. Recently, serotype 5 as well as 1 was reported as having one of the lowest observed OPA titers from all PREVNAR 13 serotypes, in which there was an associated correlation between IgG titer and OPA activity [4]. Also it was suggested that for serotype 3, a much higher serum IgG concentration would be needed for protection [5].

SUMMARY

This application provides new and improved mixed carrier, multivalent pneumococcal conjugate compositions and vaccines comprising the same. In one aspect, the mixed carrier, multivalent pneumococcal conjugate composition comprises 21 different pneumococcal capsular polysaccharide-protein conjugates, wherein each pneumococcal capsular polysaccharide-protein conjugate comprises a protein carrier conjugated to a capsular polysaccharide from a different serotype of *Streptococcus pneumoniae*, wherein the *Streptococcus pneumoniae* serotypes are selected from 1, 3, 4, 5, 6A, 6B, 7F, 8, 9N, 9V, 10A, 11A, 12F, 14, 15B, 18C, 19A, 19F, 22F, 23F and 33F, wherein the protein carrier is $CRM_{197}$ or tetanus toxoid, wherein four of the capsular polysaccharides are conjugated to tetanus toxoid and the remaining capsular polysaccharides are conjugated to CRM$_{197}$, and wherein two of the four capsular polysaccharides that are conjugated to tetanus toxoid are selected from the group consisting of serotypes 1, 3 and 5, and the remaining two capsular polysaccharides are serotypes 15B and 22F.

In one embodiment of the mixed carrier, 21-valent pneumococcal conjugate composition, the capsular polysaccharides from serotypes 1, 5, 15B and 22F are conjugated to tetanus toxoid, and the capsular polysaccharides from serotypes 3, 4, 6A, 6B, 7F, 8, 9N, 9V, 10A, 11A, 12F, 14, 18C, 19A, 19F, 23F, and 33F are conjugated to CRM$_{197}$.

In another embodiment of the mixed carrier, 21-valent pneumococcal conjugate composition, the capsular polysaccharides from serotypes 1, 3, 15B and 22F are conjugated to tetanus toxoid, and the capsular polysaccharides from serotypes 4, 5, 6A, 6B, 7F, 8, 9N, 9V, 10A, 11A, 12F, 14, 18C, 19A, 19F, 23F, and 33F are conjugated to CRM$_{197}$.

In yet another embodiment of the mixed carrier, 21-valent pneumococcal conjugate composition, the capsular polysaccharides from serotypes 3, 5, 15B and 22F are conjugated to tetanus toxoid, and the capsular polysaccharides from serotypes 1, 4, 6A, 6B, 7F, 8, 9N, 9V, 10A, 11A, 12F, 14, 18C, 19A, 19F, 23F, and 33F are conjugated to CRM$_{197}$.

In another aspect, this application provides a mixed carrier, multivalent pneumococcal conjugate composition, comprising 21 different pneumococcal capsular polysaccharide-protein conjugates, wherein each pneumococcal capsular polysaccharide-protein conjugate comprises a protein carrier conjugated to a capsular polysaccharide from a different serotype of *Streptococcus pneumoniae*, wherein the *Streptococcus pneumoniae* serotypes are selected from 1, 3, 4, 5, 6A, 6B, 7F, 8, 9N, 9V, 10A, 11A, 12F, 14, 15B, 18C, 19A, 19F, 22F, 23F and 33F, wherein the protein carrier is CRM$_{197}$ or tetanus toxoid, wherein three of the capsular polysaccharides are conjugated to tetanus toxoid and the remaining capsular polysaccharides are conjugated to CRM$_{197}$, and wherein the three capsular polysaccharides that are conjugated to tetanus toxoid are selected from the group consisting of serotypes 1, 3, 5, 15B and 22F. In certain embodiments, two of the three capsular polysaccharides that are conjugated to tetanus toxoid are selected from the group consisting of serotypes 1, 3 and 5, and the remaining capsular polysaccharide conjugated to tetanus toxoid is serotype 15B or 22F In some embodiments, the mixed carrier, multivalent pneumococcal conjugate composition further comprises an adjuvant, such as an aluminum-based adjuvant, including, but not limited to aluminum phosphate, aluminum sulfate, and aluminum hydroxide.

Another aspect is directed to the use of the mixed carrier, 21-valent pneumococcal conjugate composition as a vaccine.

Yet another aspect is directed to a vaccine comprising the mixed carrier, 21-valent pneumococcal conjugate composition and a pharmaceutically acceptable excipient.

Yet another aspect is directed to a method for prophylaxis of *Streptococcus pneumoniae* infection or disease in a subject, such as a human, the method comprising administering a prophylactically effective amount of the mixed carrier, 21-valent pneumococcal conjugate compositions or a vaccine comprising the same to the subject.

In certain embodiments, the subject is a human who is at least 50 years old and the disease is pneumonia or invasive pneumococcal disease (IPD).

In other embodiments, the subject is a human who is at least 6 weeks old and the disease is pneumonia, invasive pneumococcal disease (IPD), or acute otitis media (AOM).

In some embodiments, the human subject is 6 weeks to 5 years of age. In other embodiments, the human subject is 2 to 15 months of age or 6 to 17 years of age.

In certain embodiments, the mixed carrier, 21-valent pneumococcal conjugate composition or vaccine is administered by intramuscular injection. In certain embodiments, the mixed carrier, 21-valent pneumococcal conjugate composition or vaccine is administered as part of an immunization series.

Yet another aspect is directed to an immunogenic conjugate of *Streptococcus pneumoniae* serotype 9N, which contains: a serotype 9N capsular saccharide from *Streptococcus pneumoniae*; and a carrier protein bound to the capsular saccharide, wherein the carrier protein is CRM$_{197}$. In certain embodiments of the immunogenic serotype 9N conjugate, the mixed carrier, multivalent pneumococcal conjugate compositions and vaccines (and methods/uses of the same), the serotype 9N saccharide may be bound to CRM$_{197}$ to form a conjugate in a state where it is activated to have a degree of oxidation of 2-19 or 5-10 and a molecular weight of 200-700 kDa. In certain embodiments of the immunogenic serotype 9N conjugate, the mixed carrier, multivalent pneumococcal conjugate compositions and vaccines (and methods/uses of the same), the immunogenic serotype 9N conjugate may have a molecular weight of 500-4,000 kDa.

In certain embodiments of the immunogenic serotype 9N conjugate, the mixed carrier, multivalent pneumococcal conjugate compositions and vaccines (and methods/uses of the same), the ratio of the serotype 9N capsular saccharide to the carrier protein in the serotype 9N immunogenic conjugate is 0.1-5 (w/w). In certain embodiments, the ratio is 0.5-2.5.

In certain embodiments of the immunogenic serotype 9N conjugate, the mixed carrier, multivalent pneumococcal conjugate compositions and vaccines (and methods/uses of the same), 15-60% of the immunogenic serotype 9N conjugate may have a K$_d$ of 0.3 or below in a CL-4B column.

In certain embodiments of the immunogenic serotype 9N conjugate, the mixed carrier, multivalent pneumococcal conjugate compositions and vaccines (and methods/uses of the same), the immunogenic serotype 9N conjugate has been prepared with a serotype 9N polysaccharide that has been activated to achieve a degree of oxidation of 2-19. In certain embodiments, the immunogenic serotype 9N conjugate has been prepared with a serotype 9N polysaccharide that has been activated to achieve a degree of oxidation of 5-10.

In certain embodiments of the immunogenic serotype 9N conjugate, the mixed carrier, multivalent pneumococcal conjugate compositions and vaccines (and methods/uses of the same), when the *Streptococcus pneumoniae* serotype 9N saccharide is conjugated with the CRM$_{197}$ by adding 0.02-0.19 μg of periodate per 1 μg of sugar, the conjugate may have a molecular weight of 500-4,000 kDa, a molecular weight distribution of 15-60% (K$_d \le 0.3$) and a saccharide/protein ratio of 0.5-2.5.

In yet another aspect, the present disclosure also provides a method for preparing an immunogenic conjugate of *Streptococcus pneumoniae* serotype 9N, the method comprising:

(a) lysing a bacterial cell producing *Streptococcus pneumoniae* serotype 9N capsular polysaccharide by fermenting the same;

(b) purifying *Streptococcus pneumoniae* serotype 9N capsular saccharide from the lysed cell;

(c) activating the *Streptococcus pneumoniae* serotype 9N capsular polysaccharide by reacting with an oxidizing agent to achieve a degree of oxidation of 2-19 or 5-10; and (d) forming a conjugate of the *Streptococcus pneumoniae* serotype 9N capsular saccharide bound to $CRM_{197}$ by mixing the activated saccharide with $CRM_{197}$.

In certain embodiments, the $CRM_{197}$ mixed in the step (d) may be reacted with a reducing agent to form the conjugate with the activated *Streptococcus pneumoniae* serotype 9N capsular polysaccharide. In certain embodiments, in step (c), 0.02-0.19 µg of periodate may be reacted with 1 µg of the *Streptococcus pneumoniae* serotype 9N capsular polysaccharide at 20-25° C. for 15-20 hours.

In certain embodiments, the *Streptococcus pneumoniae* serotype 9N capsular polysaccharide reacted with the oxidizing agent in step (c) may have a molecular weight of 400-900 kDa. In certain embodiments, the activated *Streptococcus pneumoniae* serotype 9N capsular polysaccharide mixed with the $CRM_{197}$ in step (d) may have a molecular weight of 200-700 kDa. In certain embodiments, the immunogenic conjugate of *Streptococcus pneumoniae* serotype 9N may have a molecular weight of 500-4,000 kDa. In certain embodiments, an initial input ratio of the $CRM_{197}$ to the activated serotype 9N capsular saccharide (carrier $CRM_{197}$:saccharide) may be 0.5-2.5:1. In certain embodiments, at least 15-60% of the immunogenic conjugate may have a $K_d$ of 0.3 or below as measured in a CL-4B column.

In certain embodiments, when the *Streptococcus pneumoniae* serotype 9N polysaccharide of the present disclosure is conjugated with the $CRM_{197}$ by adding 0.02-0.19 µg of periodate per 1 µg of sugar, the immunogenic conjugate has a molecular weight of 500-4,000 kDa, a molecular weight distribution of 15-60% ($K_d \leq 0.3$) as measured in a CL-4B column and a $CRM_{197}$/polysaccharide ratio of 0.5-2.5.

The foregoing and other objects, features, and advantages of the mixed carrier, 21-valent pneumococcal conjugate compositions will become more apparent from the following detailed description.

Definitions

In order for the present disclosure to be more readily understood, certain terms are first defined below. Additional definitions for the following terms and other terms may be set forth through the specification.

As used in this specification and the appended claims, the singular forms "a," "an," and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Administer: As used herein, "administering" a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intradermal.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Conjugate: As used herein, and understood from the proper context, the terms "conjugate(s)" or "glycoconjugate(s)" refer to a *Streptococcus pneumoniae* polysaccharide conjugated to a carrier protein using any covalent or non-covalent bioconjugation strategy.

Degree of oxidation: As used herein, the term "degree of oxidation" (DO) refers to the number of sugar repeat units per aldehyde group generated when a purified or sized saccharide is activated with an oxidizing agent. The degree of oxidation of a saccharide can be determined using routine methods known to those of ordinary skill in the art.

Excipient: As used herein, the term "excipient" refers to a non-therapeutic agent that may be included in a composition, for example to provide or contribute to a desired consistency or stabilizing effect.

Mixed carrier: As used herein, a mixed carrier, pneumococcal conjugate composition refers to a pneumococcal conjugate composition having more than one type of protein carrier.

Multivalent: As used herein, the term "multivalent" refers to a pneumococcal conjugate composition having pneumococcal capsular polysaccharides from more than one *Streptococcus pneumoniae* serotype.

Mixed carrier, 21-valent pneumococcal conjugate composition: As used herein, the term "mixed carrier, 21-valent pneumococcal conjugate composition(s)" refers to a composition comprising or consisting of 21 different pneumococcal capsular polysaccharide-protein conjugates, wherein each pneumococcal capsular polysaccharide-protein conjugate comprises a protein carrier conjugated to a capsular polysaccharide from a different serotype of *Streptococcus pneumoniae*, wherein the *Streptococcus pneumoniae* serotypes are 1, 3, 4, 5, 6A, 6B, 7F, 8, 9N, 9V, 10A, 11A, 12F, 14, 15B, 18C, 19A, 19F, 22F, 23F, and 33F, wherein the protein carrier is $CRM_{197}$ or tetanus toxoid, wherein 1) wherein three of the capsular polysaccharides are conjugated to tetanus toxoid and the remaining capsular polysaccharides are conjugated to $CRM_{197}$, and wherein two of the three capsular polysaccharides that are conjugated to tetanus toxoid are selected from the group consisting of serotypes 1, 3 and 5, and the remaining capsular polysaccharide is serotype 15B or 22F; or 2) wherein four of the capsular polysaccharides are conjugated to tetanus toxoid and the remaining capsular polysaccharides are conjugated to $CRM_{197}$, and wherein two of the four capsular polysaccharides that are conjugated to tetanus toxoid are selected from the group consisting of serotypes 1, 3 and 5, and the remaining two capsular polysaccharides are serotypes 15B and 22F. In some embodiments, the capsular polysaccharides from serotypes 1, 5, 15B and 22F are conjugated to tetanus toxoid, and the remaining capsular polysaccharides are conjugated to $CRM_{197}$. In another embodiment, the capsular polysaccharides from serotypes 1, 3, 15B and 22F are conjugated to tetanus toxoid, and the capsular polysaccharides from the remaining serotypes are conjugated to $CRM_{197}$. In yet another embodiment, the capsular polysaccharides from serotypes 3, 5, 15B and 22F are conjugated to tetanus toxoid, and the remaining capsular polysaccharides are conjugated to $CRM_{197}$.

Molecular weight: Unless specified otherwise, as used herein, the term "molecular weight" of a capsular saccharide or a capsular saccharide-carrier protein conjugate refers to the average molecular weight calculated by size exclusion chromatography (SEC) in combination with multi-angle laser light scattering (MALLS).

Pharmaceutically acceptable excipient: The pharmaceutically acceptable excipients useful in this disclosure are conventional. Remington's Pharmaceutical Sciences, by E. W. Martin, Mack Publishing Co., Easton, PA, 15$^{th}$ Edition (1975), describes compositions and formulations suitable for pharmaceutical delivery of one or more therapeutic compositions, including vaccines, and additional pharmaceutical agents. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In general, the nature of the excipient will depend on the particular mode of administration being employed. For instance, parenteral formulations usually comprise injectable fluids that include pharmaceutically and physiologically acceptable fluids such as water, physiological saline, balanced salt solutions, buffers, aqueous dextrose, glycerol or the like as a vehicle. For solid compositions (for example, powder, pill, tablet, or capsule forms), conventional non-toxic solid excipients can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, a surface active agent, preservatives, and pH buffering agents and the like, for example sodium acetate or sorbitan monolaurate.

Prophylactically Effective Amount: As defined herein, the term "a prophylactically effective amount" or "a prophylactically effective dose" refers to the amount or dose required to induce an immune response sufficient to delay onset and/or reduce in frequency and/or severity one or more symptoms caused by an infection with *Streptococcus pneumoniae*.

Prophylaxis: The term "prophylaxis," as used herein, refers to avoidance of disease manifestation, a delay of onset, and/or reduction in frequency and/or severity of one or more symptoms of a particular disease, disorder or condition (e.g., infection with *Streptococcus pneumoniae*). In some embodiments, prophylaxis is assessed on a population basis such that an agent is considered to provide prophylaxis against a particular disease, disorder or condition if a statistically significant decrease in the development, frequency, and/or intensity of one or more symptoms of the disease, disorder or condition is observed in a population susceptible to the disease, disorder, or condition.

Subject: As used herein, the term "subject" means any mammal, including mice, rabbits, and humans. In certain embodiments the subject is an adult, an adolescent or an infant. In some embodiments, terms "individual" or "patient" are used and are intended to be interchangeable with "subject."

DETAILED DESCRIPTION

The following description of the disclosed embodiment(s) and Examples is merely exemplary in nature and is in no way intended to limit the invention, its application, or uses.

This application provides new and improved mixed carrier, multivalent pneumococcal conjugate compositions and vaccines comprising the same. While the protein carrier, CRM$_{197}$, has previously been used in single carrier, pneumococcal conjugate vaccines, this application describes the use of CRM$_{197}$ in a mixed carrier, pneumococcal conjugate vaccine. In particular, this application describes the combined use of CRM$_{197}$ and tetanus toxoid as carrier proteins for specific pneumococcal serotypes in multivalent pneumococcal conjugate compositions and vaccines.

As discussed above, the immunogenicity of different capsular polysaccharide conjugates may vary depending on the pneumococcal serotype and carrier protein used. This application describes the successful conjugation of serotype 3 to tetanus toxoid as part of a mixed carrier vaccine, notwithstanding previous teachings that serotype 3 was more immunogenic when conjugated to diphtheria toxoid rather than tetanus toxoid [6]. This application also describes the successful conjugation of serotypes 1, 5, 15B, and 22F to tetanus toxoid as part of a mixed carrier vaccine. It also discloses the unexpected finding that the antibody response to serotype 3 conjugated to tetanus toxoid in a mixed carrier, multi-valent, for example 21-valent, pneumococcal conjugate composition was about 4.5 fold higher than when serotype 3 was conjugated to CRM$_{197}$ in a single carrier, 13-valent pneumococcal conjugate composition (PREVNAR 13).

Further, the unexpected finding was not limited to serotype 3 but was also observed for other serotypes conjugated to tetanus toxoid in a mixed carrier, multi-valent pneumococcal conjugate composition. For example, as shown in the Examples, conjugation of serotypes 1 and 5 or 3 and 5 to tetanus toxoid in a mixed carrier, pneumococcal conjugate composition with the remaining serotypes conjugated to CRM$_{197}$ (e.g., PCV21(1/5/15B/22F)-TT, and PCV21(3/5/15B/22F)-TT) consistently induced significantly enhanced antibody responses to the serotypes conjugated to tetanus toxoid as compared to the antibody responses (IgG response or MOPA titers) against the same serotypes conjugated to CRM$_{197}$ in a single carrier, pneumococcal conjugate composition (PREVNAR 13).

Tetanus toxoid is significantly larger than CRM$_{197}$. Therefore, conjugating three or four of serotypes 1, 3, 5, 15B, and 22F to tetanus toxoid as part of a mixed carrier vaccine results in a reduced polysaccharide to carrier ("PS/C") ratio for those serotypes conjugated to tetanus toxoid as compared to the PS/C ratio of those same serotypes conjugated to a single carrier that is smaller than tetanus toxoid, such as CRM$_{197}$. In this way, the mixed carrier approach described in this application can be used to lower the PS/C ratios for one or more of serotypes 1, 3, 5, 15B, or 22F.

The mixed carrier, 21-valent pneumococcal conjugate compositions described in this application also include pneumococcal serotypes not currently covered by the three pneumococcal conjugate vaccines currently available on the global market: PREVNAR (called Prevenar in some countries), SYNFLORIX and PREVNAR 13. Disease caused by pneumococcal serotypes not currently covered is on the rise, due, in part, to the development of antibacterial resistance, the increased number of immunocompromised patients, and lack of immune pressure. For example, none of the currently available pneumococcal conjugate vaccines includes serotype 9N. In addition, none of the currently available pneumococcal conjugate vaccines includes serotypes 8, 10A, 11A, 12F, 15B, 22F and 33F. The present disclosure demonstrates the successful implementation of serotypes 8, 9N, 10A, 11A, 12F, 15B, 22F and 33F into a mixed carrier (tetanus toxoid and CRM$_{197}$), pneumococcal conjugate vaccine, as well as serotype 9N induced antibody responses that were about 40- to 50-fold higher than PREVNAR13.

Pneumococcal Polysaccharide Serotype 9N

The serotype 9N polysaccharide may be obtained directly from the bacteria by using an isolation procedure known to those of ordinary skill in the art (including, but not limited to, the methods disclosed in US Patent Application Publication No. 2006/0228380). In addition, the saccharide can be produced using synthetic protocols.

The serotype 9N *Streptococcus pneumoniae* strain may be obtained from established culture collections (e.g., the Streptococcal Reference Laboratory of the Centers for Disease Control and Prevention (Atlanta, Georgia)) or clinical specimens.

The bacterial cell is typically grown in a medium, such as a soy-based medium. Following fermentation of the bacterial cell producing *Streptococcus pneumoniae* serotype 9N capsular polysaccharide, the bacterial cell is lysed to produce a cell lysate. Then, the serotype 9N polysaccharide may be isolated from the cell lysate using purification techniques known in the art, including centrifugation, depth filtration, precipitation, ultrafiltration, treatment with activated carbon, diafiltration and/or column chromatography (including, but not limited to, the methods disclosed in US Patent Application Publication No. 2006/0228380). The purified serotype 9N capsular polysaccharide may be used for preparation of an immunogenic conjugate. The serotype 9N capsular polysaccharide obtained by purification of the serotype 9N polysaccharide from the *Streptococcus pneumoniae* lysate and optionally by sizing of the purified polysaccharide may be characterized by different parameters including, for example, the molecular weight (MW) of the serotype 9N capsular polysaccharide.

In certain embodiments, embodiments, the purified polysaccharide purified from the *Streptococcus pneumoniae* serotype 9N before conjugation has a molecular weight of 5-5,000 kDa. In certain embodiments, the serotype 9N capsular polysaccharide before conjugation has a molecular weight of 50-1,000 kDa. In certain embodiments, the serotype 9N capsular polysaccharide before conjugation has a molecular weight of 70-900 kDa. In certain embodiments, the serotype 9N capsular polysaccharide before conjugation has a molecular weight of 100-800 kDa. In certain embodiments, the purified serotype 9N capsular polysaccharide may be activated prior to conjugation to have a molecular weight of 50-800 kDa, 80-780 kDa, 100-770 kDa, 120-760 kDa, 140-750 kDa, 150-740 kDa, 160-730 kDa, 170-735 kDa, 180-720 kDa, 190-710 kDa, 200-700 kDa, 220-690 kDa, 240-680 kDa, 260-670 kDa, 270-660 kDa or similar molecular weight ranges. Any whole number within any of the above ranges is contemplated as an embodiment of the present disclosure.

The activated serotype 9N polysaccharide may be characterized by a degree of oxidation and molecular weight. In certain embodiments, the activated serotype 9N polysaccharide may have a degree of oxidation of 0.5-25, 0.6-23, 0.8-21, 1-20.8, 1.1-20.5, 1.2-20.3, 1.3-20, 1.4-19.5, 1.5-19.3, 1.6-19.2, 1.7-19.1 2-19, 3-18, 4-15, or 5-10.

The polysaccharide may become slightly reduced in size during a normal purification procedure. Additionally, as described in the present disclosure, the polysaccharide may be subjected to sizing before conjugation. The molecular weight range mentioned above refers to that of the purified polysaccharide after the final sizing step (e.g., after purification, hydrolysis and activation) before conjugation.

Mixed Carrier, Multivalent Pneumococcal Conjugate Compositions and Methods of Making the Same This disclosure provides a mixed carrier, multivalent pneumococcal conjugate composition comprising or consisting of 21 different pneumococcal capsular polysaccharide-protein conjugates, wherein each pneumococcal capsular polysaccharide-protein conjugate comprises a protein carrier conjugated to a capsular polysaccharide from a different serotype of *Streptococcus pneumoniae*, wherein the *Streptococcus pneumoniae* serotypes are 1, 3, 4, 5, 6A, 6B, 7F, 8, 9N, 9V, 10A, 11A, 12F, 14, 15B, 18C, 19A, 19F, 22F, 23F, and 33F, wherein the protein carrier is $CRM_{197}$ or tetanus toxoid, wherein 3-4 of the capsular polysaccharides are conjugated to tetanus toxoid and the remaining capsular polysaccharides are conjugated to $CRM_{197}$, and wherein the 3-4 capsular polysaccharides that are conjugated to tetanus toxoid are selected from the group consisting of serotypes 1, 3, 5, 15B, and 22F. In certain embodiments, three of the capsular polysaccharides are conjugated to tetanus toxoid and the remaining capsular polysaccharides are conjugated to $CRM_{197}$. In certain embodiments, four of the capsular polysaccharides are conjugated to tetanus toxoid and the remaining capsular polysaccharides are conjugated to $CRM_{197}$.

In one aspect, this disclosure provides a mixed carrier, multivalent pneumococcal conjugate composition comprising or consisting of 21 different pneumococcal capsular polysaccharide-protein conjugates, wherein each pneumococcal capsular polysaccharide-protein conjugate comprises a protein carrier conjugated to a capsular polysaccharide from a different serotype of *Streptococcus pneumoniae*, wherein the *Streptococcus pneumoniae* serotypes are 1, 3, 4, 5, 6A, 6B, 7F, 8, 9N, 9V, 10A, 11A, 12F, 14, 15B, 18C, 19A, 19F, 22F, 23F, and 33F, wherein the protein carrier is $CRM_{197}$ or tetanus toxoid, wherein four of the capsular polysaccharides are conjugated to tetanus toxoid and the remaining capsular polysaccharides are conjugated to $CRM_{197}$, and wherein two of the four capsular polysaccharides that are conjugated to tetanus toxoid are selected from the group consisting of serotypes 1, 3 and 5, and the remaining two capsular polysaccharides are serotypes 15B and 22F.

In one embodiment, the capsular polysaccharides from serotypes 1, 5, 15B and 22F are conjugated to tetanus toxoid, and the remaining capsular polysaccharides are conjugated to $CRM_{197}$. In another embodiment, the capsular polysaccharides from serotypes 1, 3, 15B and 22F are conjugated to tetanus toxoid, and the remaining capsular polysaccharides are conjugated to $CRM_{197}$. In yet another embodiment, the capsular polysaccharides from serotypes 3, 5, 15B and 22F are conjugated to tetanus toxoid, and the remaining capsular polysaccharides are conjugated to $CRM_{197}$.

In a polysaccharide-protein conjugate vaccine, a carrier protein is conjugated to a polysaccharide antigen primarily to help enhance the immune response (e.g. antibody response) to the polysaccharide antigen. Carrier proteins are preferably proteins that are non-toxic. Carrier proteins should be amenable to conjugation with a pneumococcal polysaccharide using standard conjugation procedures, as discussed in further detail below. The carrier proteins used in the mixed carrier, 21-valent pneumococcal conjugate compositions are tetanus toxoid (TT) and $CRM_{197}$, each of which has been used in the design of pneumococcal conjugate vaccines but never in the same, mixed carrier vaccine.

$CRM_{197}$ is a non-toxic variant (i.e., toxoid) of diphtheria toxin that retains the immunologic properties of the wild type diphtheria toxin. $CRM_{197}$ differs from the wild type diphtheria toxin at a single base in the structural gene, which gives rise to a single amino acid substitution from glutamic acid to glycine. $CRM_{197}$ is typically isolated from cultures of *Corynebacterium diphtheria* strain C7 (0197) grown on casamino acids and yeast extract-based medium. $CRM_{197}$ may be purified through ultra-filtration, ammonium sulfate precipitation, and ion-exchange chromatography. Alternatively, $CRM_{197}$ can be prepared recombinantly in accordance with U.S. Pat. No. 5,614,382, which is hereby incorporated by reference in its entirety. $CRM_{197}$ has been used in the design of pneumococcal conjugate vaccines but never as part of a mixed carrier vaccine.

Tetanus toxoid is prepared and used worldwide for large-scale immunization against tetanus (or lockjaw) caused by *Clostridium tetani*. Tetanus toxoid is also used both singly and in combination with diphtheria and/or pertussis vaccines. The parent protein, tetanus toxin, is generally obtained in cultures of *Clostridium tetani*. Tetanus toxin is a protein of about 150 kDa and consists of two subunits (about 100 kDa and about 50 kDa) linked by a disulfide bond. The toxin is typically detoxified with formaldehyde and can be purified from culture filtrates using known methods, such as ammonium sulfate precipitation (see, e.g., [7], [8]) or chromatography techniques, as disclosed, for example, in WO 1996/025425. Tetanus toxin may also be inactivated by recombinant genetic means.

Tetanus toxoid has also been used as a carrier protein in other vaccines, including pneumococcal conjugate vaccines. But using tetanus toxin in a mixed carrier, pneumococcal conjugate vaccine in combination with $CRM_{197}$ is new. The art also teaches away from conjugating serotype 3 to tetanus toxoid in a mixed carrier, pneumococcal conjugate vaccine because serotype 3 was shown to be more immunogenic when conjugated to diphtheria toxoid as compared to tetanus toxoid [6].

The pneumococcal capsular polysaccharides used in the compositions and vaccines described herein, including the capsular polysaccharides from serotypes 1, 3, 4, 5, 6A, 6B, 7F, 8, 9N, 9V, 10A, 11A, 12F, 14, 15B, 18C, 19A, 19F, 22F, 23F, and 33F, may be prepared from *Streptococcus pneumoniae* using any available technique, including standard techniques known to one of ordinary skill in the art, including, for example, those disclosed in WO 2006/110381, WO 2008/118752, WO 2006/110352, and U.S. Patent App. Pub. Nos. 2006/0228380, 2006/0228381, 2007/0184071, 2007/0184072, 2007/0231340, 2008/0102498 and 2008/0286838, all of which are incorporated by reference in their entireties. For example, each pneumococcal capsular polysaccharide serotype may be grown in culture medium (e.g., a soy-based medium). The cells are lysed, and individual polysaccharides may be purified from the lysate through centrifugation, precipitation, ultra-filtration, and/or column chromatography. In addition, the pneumococcal capsular polysaccharide can be produced using synthetic protocols.

Capsular polysaccharides of *Streptococcus pneumoniae* comprise repeating oligosaccharide units, which may contain up to 8 sugar residues. A capsular saccharide antigen may be a full length polysaccharide, or it may be reduced in size (e.g., a single oligosaccharide unit, or a shorter than native length saccharide chain of repeating oligosaccharide units). The size of capsular polysaccharides may be reduced by various methods known in the art, such as acid hydrolysis treatment, hydrogen peroxide treatment, sizing by a high pressure homogenizer, optionally followed by a hydrogen peroxide treatment to generate oligosaccharide fragments, or microfluidization.

The pneumococcal conjugate of each of the serotypes may be prepared by conjugating a capsular polysaccharide of each serotype to a carrier protein. The different pneumococcal conjugates may be formulated into a composition, including a single dosage formulation.

To prepare a polysaccharide-protein conjugate, the capsular polysaccharides prepared from each pneumococcal serotype may be chemically activated so that the capsular polysaccharides may react with a carrier protein. Once activated, each capsular polysaccharide may be separately conjugated to a carrier protein to form a glycoconjugate. The chemical activation of the polysaccharides and subsequent conjugation to the carrier protein may be achieved by conventional methods. For example, vicinal hydroxyl groups at the end of the capsular polysaccharides can be oxidized to aldehyde groups by oxidizing agents such as periodates (including sodium periodate, potassium periodate, or periodic acid), as disclosed, for example, in U.S. Pat. Nos. 4,365,170, 4,673,574 and 4,902,506, which are hereby incorporated by reference in their entireties. The periodate randomly oxidizes the vicinal hydroxyl group of a carbohydrate to form a reactive aldehyde group and causes cleavage of a C—C bond. The term "periodate" includes both periodate and periodic acid. This term also includes both metaperiodate ($IO_{4-}$) and orthoperiodate ($IO_{65-}$). The term "periodate" also includes various salts of periodate including sodium periodate and potassium periodate. In certain embodiments, the polysaccharide may be oxidized in the presence of sodium metaperiodate.

In certain embodiments, the periodate may be used in an amount of about 0.03-0.17 μg per 1 μg of polysaccharide. In certain embodiments, the periodate may be used in an amount of about 0.025-0.18 μg or about 0.02-0.19 μg per 1 μg of polysaccharide. The saccharide may be activated as desired within the above range. Outside the range, the effect may be unsatisfactory.

Polysaccharides may also be activated with 1-cyano-4-dimethylamino pyridinium tetrafluoroborate (CDAP) to form a cyanate ester. The activated polysaccharide is then coupled directly or via a spacer or linker group to an amino group on the carrier protein.

For example, the spacer could be cystamine or cysteamine to give a thiolated polysaccharide which could be coupled to the carrier via a thioether linkage obtained after reaction with a maleimide-activated carrier protein (for example using N-[y-maleimidobutyrloxy]succinimide ester (GMBS)) or a haloacetylated carrier protein (for example using iodoacetimide, N-succinimidyl bromoacetate (SBA; SIB), N-succinimidyl(4-iodoacetyl)aminobenzoate (SIAB), sulfosuccinimidyl(4-iodoacetyl)aminobenzoate (sulfo-SIAB), N-succinimidyl iodoacetate (SIA) or succinimidyl 3-[bromoacetamido]proprionate (SBAP)). Preferably, the cyanate ester (optionally made by COAP chemistry) is coupled with hexane diamine or adipic acid dihydrazide (AOH) and the amino-derivatized saccharide is conjugated to the carrier protein using carbodiimide (e.g., EDAC or EDC) chemistry via a carboxyl group on the protein carrier. Such conjugates are described for example in WO 93/15760, WO 95/08348 and WO 96/129094, all of which are hereby incorporated by reference in their entireties.

The conjugation of the activated capsular polysaccharides and the carrier proteins may be achieved, for example, by reductive amination, as described, for example, in U.S. Patent Appl. Pub. Nos. 2006/0228380, 2007/0231340, 2007/0184071 and 2007/0184072, WO 2006/110381, WO 2008/079653, and WO 2008/143709, all of which are incorporated by reference in their entireties. For example, the activated capsular polysaccharides and the carrier protein may be reacted with a reducing agent to form a conjugate. Reducing agents which are suitable include borohydrides, such as sodium cyanoborohydride, borane-pyridine, sodium triacetoxyborohydride, sodium borohydride, or borohydride exchange resin. At the end of the reduction reaction, there may be unreacted aldehyde groups remaining in the conjugates. The unreacted aldehyde groups may be capped using a suitable capping agent, such as sodium borohydride ($NaBH_4$). In an embodiment, the reduction reaction is carried out in aqueous solvent. In another embodiment the reaction is carried out in aprotic solvent. In an embodiment, the reduction reaction is carried out in DMSO (dimethylsulfoxide) or in DMF (dimethylformamide) solvent. Other possible reducing agents include, but are not limited to, amine-boranes such as pyridine-borane, 2-picoline-borane, 2,6-diborane-methanol, dimethylamine-borane, t-BuMeiPrN—BH3, benzylamine-BH3 or 5-ethyl-2-methylpyridine-borane (PEMB).

The activated capsular polysaccharides may be conjugated directly to the carrier protein or indirectly through the use of a spacer or linker, such as a bifunctional linker. The linker is optionally heterobifunctional or homobifunctional, having for example a reactive amino group and a reactive carboxylic acid group, 2 reactive amino groups or two reactive carboxylic acid groups.

Other suitable techniques for conjugation use carbodiimides, hydrazides, active esters, norborane, p-nitrobenzoic acid, N-hydroxysuccinimide, S—NHS, EDC, TSTU, as described, for example, in International Patent Application Publication No. WO 98/42721, which is incorporated by reference in their entirety. Conjugation may involve a carbonyl linker which may be formed by reaction of a free hydroxyl group of the saccharide with 1,1'-carbonyldiimidazole (CDl) (see Bethell et al. (1979) J. Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDl carbamate intermediate with an amino group on a protein.

The ratio of polysaccharide to carrier protein for pneumococcal conjugate vaccines is typically in the range 0.3-3.0 (w/w) but can vary with the serotype. The ratio can be determined either by independent measurement of the amounts of protein and polysaccharide present, or by methods that give a direct measure of the ratio known in the art. Methods including $^1$H NMR spectroscopy or SEC-HPLC-UV/RI with dual monitoring (e.g. refractive index and UV, for total material and protein content respectively) can profile the saccharide/protein ratio over the size distribution of conjugates, as well as by SEC-HPLC-MALLS or MALDI-TOF-MS.

The polysaccharide-protein conjugates thus obtained may be purified and enriched by a variety of methods. These methods include concentration/diafiltration, column chromatography, and depth filtration. The purified polysaccharide-protein conjugates are combined to formulate a mixed carrier, 21-valent pneumococcal conjugate composition, which can be used as a vaccine.

Formulation of a vaccine composition can be accomplished using art-recognized methods. A vaccine composition is formulated to be compatible with its intended route of administration. The individual pneumococcal capsular polysaccharide-protein conjugates can be formulated together with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In some embodiments, the mixed carrier, 21-valent pneumococcal conjugate composition further comprises an adjuvant. As used herein, an "adjuvant" refers to a substance or vehicle that non-specifically enhances the immune response to an antigen. Adjuvants can include a suspension of minerals (alum, aluminum salts, such as aluminum hydroxide, aluminum phosphate, aluminum sulfate, aluminum hydroxy phosphate sulfate, etc.) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as lipids and costimulatory molecules. Exemplary biological adjuvants include ASO4 [9], IL-2, RANTES, GM-CSF, TNF-α, IFN-γ, G-CSF, LFA-3, CD72, B7-1, B7-2, OX-40L and 41 BBL.

In some embodiments, the adjuvant is an aluminum-based adjuvant. Typically, a single 0.5 ml vaccine dose is formulated to contain about 0.1 mg to 2.5 mg of the aluminum-based adjuvant. In other embodiments, a single 0.5 ml vaccine dose is formulated to contain between 0.1 mg to 2 mg, 0.1 mg to 1 mg, 0.1 mg to 0.5 mg, 0.1 mg to 0.2 mg, 0.125 mg to 2.5 mg, 0.125 mg to 0.5 mg, 0.125 mg to 0.2 mg or 0.125 to 0.25 mg of the aluminum-based adjuvant. In certain embodiments, a single 0.5 ml vaccine dose is formulated to contain about 0.125 mg to about 0.250 mg of the aluminum-based adjuvant. In certain embodiments, a single 0.5 ml vaccine dose is formulated to contain about 0.125 mg of the aluminum-based adjuvant. In certain embodiments, a single 0.5 ml vaccine dose is formulated to contain about 0.250 mg of the aluminum-based adjuvant.

In particular embodiments, the adjuvant is selected from the group consisting of aluminum phosphate, aluminum sulfate, and aluminum hydroxide.

In particular embodiments, the adjuvant is aluminum phosphate.

In some embodiments, the composition is for use as a vaccine against an infection of *Streptococcus pneumoniae*. Characterization of Pneumococcal Capsular Polysaccharide-Protein Carrier Conjugates In certain embodiments, the polysaccharide-protein carrier conjugate may have a molecular weight of 100-10,000 kDa. In certain embodiments, the conjugate has a molecular weight of 200-9,000 kDa. In certain embodiments, the conjugate has a molecular weight of 300-8,000 kDa. In certain embodiments, the conjugate has a molecular weight of 400-7,000 kDa. In certain embodiments, the conjugate has a molecular weight of 500-6,000 kDa. In certain embodiments, the conjugate has a molecular weight of 600-5,000 kDa. In certain embodiments, the conjugate has a molecular weight of 500-4,000 kDa molecular weight. Any whole number within any of the above ranges is contemplated as an embodiment of the present disclosure.

When the molecular weight is within the above range, the conjugate may be formed stably with high yield. Also, the proportion of a free polysaccharide can be reduced. In addition, superior immunogenicity can be achieved within the above molecular weight range.

After the individual polysaccharide-protein conjugates are purified, they are compounded to formulate the immunogenic composition of the present disclosure.

The saccharide-protein conjugates of the serotypes of the present disclosure may be characterized by a ratio of the polysaccharide to the protein carrier (amount of polysaccharide/amount of protein carrier, w/w).

In certain embodiments, the ratio (w/w) of the polysaccharide to the protein carrier in the polysaccharide-protein carrier conjugate for each serotype is 0.5-2.5, 0.4-2.3, 0.3-

2.1, 0.24-2, 0.2-1.8, 0.18-1.6, 0.16-1.4, 0.14-1.2, 0.12-1 or 0.1-1 (e.g., about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4 or about 2.5).

When the ratio of the polysaccharide to the protein carrier is within the above range, the conjugate may be formed stably with high yield. Also, the proportion of a free polysaccharide can be reduced. In addition, superior immunogenicity can be achieved and the conjugate can be maintained stably without interference by other serotypes within the above range.

The conjugates and immunogenic compositions of the present disclosure may contain a free polysaccharide which is not covalently conjugated to the protein carrier but is nevertheless present in the polysaccharide-protein carrier conjugate composition. The free polysaccharide may be non-covalently associated with the polysaccharide-protein carrier conjugate (i.e., non-covalently bound to, adsorbed to, or entrapped in or by the polysaccharide-protein carrier conjugate).

In certain embodiments, the polysaccharide-protein carrier conjugate contains less than about 60%, about 50%, 45%, 40%, 35%, 30%, 25%, 20% or 15% of a free polysaccharide of each serotype based on the total amount of the polysaccharide of each serotype. In certain embodiments, the polysaccharide-protein carrier conjugate of each serotype contains less than about 60% of a free polysaccharide of each serotype based on the total amount of the polysaccharide of each serotype. In certain embodiments, the polysaccharide-protein carrier conjugate of each serotype contains less than about 50% of a free polysaccharide of each serotype based on the total amount of the polysaccharide of each serotype. In certain embodiments, the polysaccharide-protein carrier conjugate of each serotype contains less than about 40% of a free polysaccharide of each serotype based on the total amount of the polysaccharide of each serotype. In certain embodiments, the polysaccharide-protein carrier conjugate of each serotype contains less than about 30% of a free polysaccharide of each serotype based on the total amount of the polysaccharide of each serotype. In certain embodiments, the polysaccharide-protein carrier conjugate of each serotype contains less than about 25% of a free polysaccharide of each serotype based on the total amount of the polysaccharide of each serotype. In certain embodiments, the polysaccharide-protein carrier conjugate of each serotype contains less than about 20% of a free polysaccharide of each serotype based on the total amount of the polysaccharide of each serotype. In certain embodiments, the polysaccharide-protein carrier conjugate of each serotype contains less than about 15% of a free polysaccharide of each serotype based on the total amount of the polysaccharide of each serotype. In certain embodiments, the polysaccharide-protein carrier conjugate of each serotype contains less than about 10% of a free polysaccharide of each serotype based on the total amount of the polysaccharide of each serotype.

The polysaccharide-protein carrier conjugate of each serotype may also be characterized by its molecular size distribution ($K_d$). A size exclusion chromatography medium (CL-4B; cross-linked agarose beads, 4%) may be used to determine the relative molecular size distribution of the conjugate. Size exclusion chromatography (SEC) is used in a gravity-fed column to profile the molecular size distribution of the conjugate. Large molecules excluded from the pores in the medium are eluted more quickly than small molecules. A fraction collector is used to collect the column eluate. The fractions are tested colorimetrically by saccharide assay. For the determination of $K_d$, the column is calibrated to establish the fraction at which molecules are completely excluded ($V_0$; $K_d$=0) and the fraction representing the maximum retention ($V_i$; $K_d$=1). The fraction at which a specified sample attribute is reached ($V_e$) is related to $K_d$ by the expression $K_d$=($V_e$-$V_0$)/($V_i$-$V_0$).

In certain embodiments, at least 15% of the polysaccharide-protein carrier conjugate of each serotype may have a $K_d$ of 0.3 or below in a CL-4B column.

In certain embodiments, at least 20% of the polysaccharide-protein carrier conjugate of each serotype may have a $K_d$ of 0.3 or below in a CL-4B column. In certain embodiments, at least 15%, 20%, 25%, 30%, 35%, 40%, 45%, 50%, 55%, 60%, 65%, 70%, 75%, 80%, 85% or 90% of the polysaccharide-protein carrier conjugate of each serotype may have a $K_d$ of 0.3 or below in a CL-4B column. In certain embodiments, at least 60% of the polysaccharide-protein carrier conjugate of each serotype may have a $K_d$ of 0.3 or below in a CL-4B column. In certain embodiments, at least 50-80% of the polysaccharide-protein carrier conjugate of each serotype may have a $K_d$ of 0.3 or below in a CL-4B column. In certain embodiments, at least 65-80% of the polysaccharide-protein carrier conjugate of each serotype may have a $K_d$ of 0.3 or below in a CL-4B column. In certain embodiments, at least 15-60% of the saccharide-protein conjugate of each serotype may have a $K_d$ of 0.3 or below in a CL-4B column.

Prophylactic Methods and Uses

In one aspect, this disclosure provides a vaccine comprising a mixed carrier, 21-valent pneumococcal conjugate composition and a pharmaceutically acceptable excipient. In some embodiments, the pharmaceutically acceptable excipient comprises at least a buffer, such as a succinate buffer, a salt, such as sodium chloride, and/or a surface active agent, such as a polyoxyethylene sorbitan ester (e.g., polysorbate 80). In some embodiments, three or four capsular polysaccharides from specific serotypes as mentioned above are conjugated to the tetanus toxoid, and the remaining capsular polysaccharides among 1, 3, 4, 5, 6A, 6B, 7F, 8, 9N, 9V, 10A, 11A, 12F, 14, 15B, 18C, 19A, 19F, 22F, 23F, and 33F are conjugated to $CRM_{197}$ (21-valent).

In one embodiment, the capsular polysaccharides from serotypes 1, 5, 15B and 22F are conjugated to the tetanus toxoid, and the capsular polysaccharides from serotypes 3, 4, 6A, 6B, 7F, 8, 9N, 9V, 10A, 11A, 12F, 14, 18C, 19A, 19F, 23F, and 33F are conjugated to $CRM_{197}$ (21-valent).

In another embodiment, the capsular polysaccharides from serotypes 1, 3, 15B and 22F are conjugated to the tetanus toxoid, and the capsular polysaccharides from serotypes 4, 5, 6A, 6B, 7F, 8, 9N, 9V, 10A, 11A, 12F, 14, 18C, 19A, 19F, 23F, and 33F are conjugated to $CRM_{197}$ (21-valent).

In yet another embodiment, the capsular polysaccharides from serotypes 3, 5, 15B and 22F are conjugated to the tetanus toxoid, and the capsular polysaccharides from serotypes 1, 4, 6A, 6B, 7F, 8, 9N, 9V, 10A, 11A, 12F, 14, 18C, 19A, 19F, 23F, and 33F are conjugated to $CRM_{197}$ (21-valent).

In some embodiments, the vaccine elicits a protective immune response in a human subject against disease caused by *Streptococcus pneumoniae* infection.

According to a further aspect, this disclosure provides a method for prophylaxis of *Streptococcus pneumoniae* infection or disease, the method comprising administering to a human subject a prophylactically effective amount of a mixed carrier, 21-valent pneumococcal conjugate composition or a vaccine comprising the same. The mixed carrier, 21-valent pneumococcal conjugate composition or vaccine comprising the same may be administered by any route, including, for example, by a systemic or mucosal route, as described below in further detail.

In certain embodiments, the human subject is an elderly subject and the disease is pneumonia or invasive pneumococcal disease (IPD). In certain embodiments, the elderly subject is at least 50 years old. In other embodiments, the elderly subject is at least 55 years old. In yet other embodiments, the elderly subject is at least 60 years old.

In other embodiments, the human subject is an infant and the disease is pneumonia, invasive pneumococcal disease (IPD), or acute otitis media (AOM). In certain embodiments, the infant is 0-2 years. In other embodiments, the infant is 2 to 15 months.

In yet another embodiment, the human subject is 6 weeks to 17 years of age and the disease is pneumonia, invasive pneumococcal disease (IPD) or acute otitis media (AOM). In certain embodiments, the human subject is 6 weeks to 5 years of age. In other embodiments, the human subject is 5 to 17 years of age.

The amount of conjugate in each vaccine dose or the prophylactically effective amount of the mixed carrier, multivalent pneumococcal conjugate composition may be selected as an amount that induces prophylaxis without significant, adverse effects. Such an amount can vary depending upon the pneumococcal serotype. Generally, each dose may include about 0.1 µg to about 100 µg of polysaccharide, specifically, about 0.1 to 10 µg, and, more specifically, about 1 µg to about 5 µg. Optimal amounts of components for a particular vaccine can be ascertained by standard studies involving observation of appropriate immune responses in subjects. For example, the amount for vaccination of a human subject can be determined by extrapolating an animal test result. In addition, the dose can be determined empirically.

In some embodiments, the vaccine or the mixed carrier, 21-valent pneumococcal conjugate composition may be a single 0.5 ml dose formulated to contain about 1 µg to about g of each capsular polysaccharide; about 1 µg to about 30 µg of TT; about 20 µg to about 85 µg of $CRM_{197}$; and optionally about 0.1 mg to about 0.5 mg of elemental aluminum adjuvant.

In some embodiments, the vaccine or the mixed carrier, 21-valent pneumococcal conjugate composition may be a single 0.5 ml dose formulated to contain about 2 µg to about 2.5 µg of each capsular polysaccharide except serotype 6B and optionally serotype 3, which is/are present in an amount of about 4 µg to about 5 µg; about 2 µg to about 25 µg of TT; about 40 g to about 75 µg of $CRM_{197}$; and optionally about 0.1 mg to about 0.25 mg of elemental aluminum adjuvant.

In some embodiments, the vaccine or the mixed carrier, 21-valent pneumococcal conjugate composition may be a single 0.5 ml dose formulated to contain about 2.2 ag of each capsular polysaccharide except serotype 6B, which is present in an amount of about 4.4 ag.

In some embodiments, the vaccine or the mixed carrier, 21-valent pneumococcal conjugate composition may be a single 0.5 ml dose formulated to contain about 2 ag to about 2.5 ag of each of the capsular polysaccharides except for up to six capsular polysaccharides selected from the group consisting of serotypes 1, 3, 4, 5, 6B, 9V, 19A, and 19F, each of which is present in an amount of about 4 µg to about 5 µg. In one embodiment, the up to six capsular polysaccharides, present in an amount of about 4 µg to about 5 µg, are selected from the group consisting of serotypes 1, 3, 4, 6B, 9V, 19A, and 19F. In other embodiments, the vaccine or the mixed carrier, 21-valent pneumococcal conjugate composition may be a single 0.5 ml dose formulated to contain about 2.2 µg of each of the capsular polysaccharides except for up to six capsular polysaccharides selected from the group consisting of serotypes 1, 3, 4, 5, 6B, 9V, 19A, and 19F, each of which is present in an amount of about 4.4 µg. In one embodiment, the up to six capsular polysaccharides, present in an amount of about 4.4 µg, are selected from the group consisting of serotypes 1, 3, 4, 6B, 9V, 19A, and 19F.

In some embodiments, the vaccine or the mixed carrier, 21-valent pneumococcal conjugate composition may be a single 0.5 ml dose formulated to contain about 2 µg to about 2.5 µg of the capsular polysaccharides of serotypes 4, 5, 6A, 7F, 8, 9V, 9N, 10A, 11A, 12F, 14, 15B, 18C, 22F, 23F, and 33F and about 4 µg to about 5 µg of the capsular polysaccharides of serotypes 1, 3, 6B, 19A, and 19F.

In some embodiments, the vaccine or the mixed carrier, 21-valent pneumococcal conjugate composition may be a single 0.5 ml dose formulated to contain about 2 µg to about 2.5 µg of the capsular polysaccharides of serotypes 1, 5, 6A, 7F, 8, 9N, 10A, 11A, 12F, 14, 15B, 18C, 22F, 23F, and 33F and about 4 µg to about 5 µg of the capsular polysaccharides of serotypes 3, 4, 6B, 9V, 19A, and 19F.

In certain embodiments, the vaccine or the mixed carrier, 21-valent pneumococcal conjugate composition may be a single 0.5 ml dose formulated to contain about 2-2.5 µg of the capsular polysaccharides of serotypes 1, 4, 5, 6A, 7F, 8, 9V, 9N, 10A, 11A, 12F, 14, 15B, 18C, 19A, 19F, 22F, 23F, and 33F and about 4 to about 5 µg of the capsular polysaccharides of serotypes 3 and 6B.

In some embodiments, the vaccine or the mixed carrier, 21-valent pneumococcal conjugate composition may be a single 0.5 ml dose formulated to contain about 2 to about 2.5 g of the capsular polysaccharides of serotypes 1, 4, 5, 6A, 7F, 8, 9V, 9N, 10A, 11A, 12F, 14, 15B, 18C, 19A, 19F, 22F, 23F, and 33F and about 4 to about 5 µg of the capsular polysaccharides of serotype 6B and about 8 to about 9 ag of the capsular polysaccharides of serotype 3, and more preferably about 8.8 ag of the capsular polysaccharides of serotype 3.

In certain embodiments, the mixed carrier, 21-valent pneumococcal conjugate composition or vaccine comprising the same further comprises sodium chloride and sodium succinate buffer as excipients.

In some embodiments, the mixed carrier, 21-valent pneumococcal conjugate composition may be formulated into a liquid formulation in which each of the pneumococcal capsular polysaccharides of serotypes 1, 5, 15B and 22F is conjugated to TT and the capsular polysaccharides from serotypes 3, 4, 6A, 6B, 7F, 8, 9N, 9V, 10A, 11A, 12F, 14, 18C, 19A, 19F, 23F, and 33F are conjugated to $CRM_{197}$ (21-valent). Each 0.5 mL dose may be formulated into a liquid containing: about 2.2 µg of each capsular polysaccharide, except for serotype 6B at about 4.4 µg; about 2 µg to about 25 µg of TT carrier protein (only for the serotypes 1, 5, 15B and 22F) and about 40 µg to about 75 µg of $CRM_{197}$ carrier protein; about 0.125 to 0.250 mg of elemental aluminum (about 0.5 to 1.2 mg aluminum phosphate) adjuvant; and sodium chloride and sodium succinate buffer as excipients.

In some embodiments, the mixed carrier, 21-valent pneumococcal conjugate composition may be formulated into a liquid formulation in which each of the pneumococcal capsular polysaccharides of serotypes 3, 5, 15B and 22F is conjugated to TT and the capsular polysaccharides from serotypes 1, 4, 6A, 6B, 7F, 8, 9N, 9V, 10A, 11A, 12F, 14, 18C, 19A, 19F, 23F, and 33F are conjugated to $CRM_{197}$ (21-valent). In one embodiment, each 0.5 mL dose may be formulated into a liquid containing: about 2.2 µg of each capsular polysaccharide, except for serotype 6B at about 4.4 µg; about 2 µg to about 25 µg of TT carrier protein (only for the serotypes 3, 5, 15B and 22F) and about 40 µg to about 70 µg of $CRM_{197}$ carrier protein; about 0.125 mg to about 0.250 mg of elemental aluminum (about 0.5 to 1.2 mg aluminum phosphate) adjuvant; and sodium chloride and sodium succinate buffer as excipients. In another embodiment, each 0.5 mL dose may be formulated into a liquid containing: about 2.2 µg of each capsular polysaccharide, except for up to six capsular polysaccharides selected from the group consisting of serotype 1, 3, 4, 5, 6B, 9V, 19A, and 19F at about 4.4 µg; about 2 µg to about 25 µg of TT carrier protein (only for the serotypes 3, 5, 15B and 22F) and about 40 µg to about 70 µg of $CRM_{197}$ carrier protein; about 0.125 mg to about 0.250 mg of elemental aluminum (about 0.5 to 1.2 mg aluminum phosphate) adjuvant; and sodium chloride and sodium succinate buffer as excipients. In one embodiment, the up to six capsular polysaccharides at about 4.4 µg are selected from the group consisting of serotype 1, 3, 4, 6B, 9V, 19A, and 19F. In yet another embodiment, each 0.5 mL dose may be formulated into a liquid containing: about 2.2 µg of each capsular polysaccharide, except for serotypes 1, 3, 6B, 19A, and 19F at about 4.4 µg; about 2 µg to about 25 µg of TT carrier protein (only for the serotypes 3, 5, 15B and 22F) and about 40 µg to about 70 µg of $CRM_{197}$ carrier protein; about 0.125 mg to about 0.250 mg of elemental aluminum (about 0.5 to 1.2 mg aluminum phosphate) adjuvant; and sodium chloride and sodium succinate buffer as excipients.

In some embodiments, the mixed carrier, 21-valent pneumococcal conjugate composition may be formulated into a liquid formulation in which each of the pneumococcal capsular polysaccharides of serotypes 1, 3, 15B and 22F is conjugated to TT and the capsular polysaccharides from serotypes 4, 5, 6A, 6B, 7F, 8, 9N, 9V, 10A, 11A, 12F, 14, 18C, 19A, 19F, 23F, and 33F are conjugated to $CRM_{197}$ (21-valent). In one embodiment, each 0.5 mL dose may be formulated into a liquid containing: about 2.2 µg of each capsular polysaccharide, except for serotype 6B at about 4.4 µg; about 2 µg to about 25 µg of TT carrier protein (only for the serotypes 1, 3, 15B and 22F) and about 40 µg to about 75 µg of $CRM_{197}$ carrier protein; about 0.125 mg to about 0.250 mg of elemental aluminum (about 0.5 to 1.2 mg aluminum phosphate) adjuvant; and sodium chloride and sodium succinate buffer as excipients.

In some embodiments, the liquid formulation may be filled into a single dose syringe without a preservative. After shaking, the liquid formulation becomes a vaccine that is a homogeneous, white suspension ready for intramuscular administration.

The mixed carrier, 21-valent pneumococcal conjugate composition can be administered in a single injection or as part of an immunization series. For example, the mixed carrier, 21-valent pneumococcal conjugate composition can be administered 2, 3, 4, or more times at appropriately spaced intervals, such as, a 1, 2, 3, 4, 5, or 6 month interval or a combination thereof. In some embodiments, the mixed carrier, 21-valent pneumococcal conjugate composition is administered to an infant 4 times within the first 15 months of birth, including, for example, at about 2, 3, 4, and 12-15 months of age; at about 3, 4, 5, and 12-15 months of age; or at about 2, 4, 6, and 12 to 15 months of age. This first dose can be administered as early as 6 weeks of age. In another embodiment, the mixed carrier, 21-valent pneumococcal conjugate composition is administered to an infant 3 times within the first 15 months of birth, including, for example, at about 2, 4, and 11-12 months.

The mixed carrier, multivalent pneumococcal conjugate composition may also include one or more proteins from *Streptococcus pneumoniae*. Examples of *Streptococcus pneumoniae* proteins suitable for inclusion include those identified in International Patent Application WO02/083855, as well as those described in International Patent Application WO02/053761.

The mixed carrier, 21-valent pneumococcal conjugate composition can be administered to a subject via one or more administration routes known to one of ordinary skill in the art such as a parenteral, transdermal, or transmucosal, intranasal, intramuscular, intraperitoneal, intracutaneous, intravenous, or subcutaneous route and be formulated accordingly. The mixed carrier, 21-valent pneumococcal conjugate composition can be formulated to be compatible with its intended route of administration.

In some embodiments, the mixed carrier, 21-valent pneumococcal conjugate composition can be administered as a liquid formulation by intramuscular, intraperitoneal, subcutaneous, intravenous, intraarterial, or transdermal injection or respiratory mucosal injection. The mixed carrier, 21-valent pneumococcal conjugate compositions can be formulated in liquid form or in a lyophilized form. In some embodiments, injectable compositions are prepared in conventional forms, either as liquid solutions or suspensions, solid forms suitable for solution or suspension in liquid prior to injection, or as emulsions. In some embodiments, injection solutions and suspensions are prepared from sterile powders or granules. General considerations in the formulation and manufacture of pharmaceutical agents for administration by these routes may be found, for example, in *Remington's Pharmaceutical Sciences*, 19th ed., Mack Publishing Co., Easton, P A, 1995; incorporated herein by reference. At present the oral or nasal spray or aerosol route (e.g., by inhalation) are most commonly used to deliver therapeutic agents directly to the lungs and respiratory system. In some embodiments, a mixed carrier, 21-valent pneumococcal conjugate composition is administered using a device that delivers a metered dosage of composition. Suitable devices for use in delivering intradermal pharmaceutical compositions described herein include short needle devices such as those described in U.S. Pat. Nos. 4,886,499, 5,190,521, 5,328,483, 5,527,288, 4,270,537, 5,015,235, 5,141,496, 5,417,662 (all of which are incorporated herein by reference). Intradermal compositions may also be administered by devices which limit the effective penetration length of a needle into the skin, such as those described in WO1999/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO1997/37705, and WO1997/13537 (all of which are incorporated herein by reference). Also suitable are ballistic powder/particle delivery devices which use compressed gas to accelerate vaccine in powder form through the outer layers of the skin to the dermis. Additionally, conventional syringes may be used in the classical Mantoux method of intradermal administration.

Preparations for parenteral administration include sterile aqueous or nonaqueous solutions, suspensions, and emulsions. Examples of non-aqueous solvents are propylene glycol, polyethylene glycol, oils such as olive oil, and injectable organic esters such as ethyl oleate. Examples of oil include vegetable or animal oil, peanut oil, soybean oil, olive oil, sunflower oil, liver oil, synthetic oil such as marine oil, and lipids obtained from milk or eggs. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The mixed carrier, 21-valent pneumococcal conjugate composition can be formulated in the form of a unit dose vial, multiple dose vial, or pre-filled syringe. A pharmaceutically acceptable carrier for a liquid formulation includes aqueous or nonaqueous solvent, suspension, emulsion, or oil. The composition may be isotonic, hypertonic, or hypotonic. However, it is desirable that the composition for infusion or injection is basically isotonic. Thus, isotonicity or hypertonicity may be advantageous for storage of the composition. When the composition is hypertonic, the composition can be diluted to isotonicity before administration. A tonicity agent may be ionic tonicity agent such as salt or non-ionic tonicity agent such as carbohydrate. The ionic tonicity agent includes, but is not limited to, sodium chloride, calcium chloride, potassium chloride, and magnesium chloride. The nonionic tonicity agent includes, but is not limited to, sorbitol and glycerol. Preferably, at least one pharmaceutically acceptable buffer is included. For example, when the composition is an infusion or injection, it is preferable to be formulated in a buffer with a buffering capacity at pH 4 to pH 10, such as pH 5 to pH 9, or, pH 6 to pH 8. The buffer may be selected from those suitable for United States Pharmacopeia (USP). For example, the buffer can be selected from the group consisting of a monobasic acid, such as acetic acid, benzoic acid, gluconic acid, glyceric acid, and lactic acid; a dibasic acid, such as aconitic acid, adipic acid, ascorbic acid, carbonic acid, glutamic acid, malic acid, succinic acid, and tartaric acid; a polybasic acid such as citric acid and phosphoric acid; and a base such as ammonia, diethanolamine, glycine, triethanolamine, and TRIS.

The mixed carrier, 21-valent pneumococcal conjugate composition may comprise a surface active agent. Examples of the surface active agent include, but are not limited to, polyoxyethylene sorbitan ester (generally referred to as Tweens), in particular, polysorbate 20 and polysorbate 80; copolymers (such as DOWFAX) of ethylene oxide (EO), propylene oxide (PO), butylenes oxide (BO); octoxynols with different repeats of ethoxy(oxy-1,2-ethanediyl) group, in particular, octoxynol-9 (Triton-100); ethylphenoxypolyethoxyethanol (IGEPAL CA-630/NP-40); phospholipid such as lecithin; nonylphenol ethoxylate such as TERGITOL NP series; lauryl, cetyl, stearyl, oleyl alcohol-derived polyoxyethylene fatty ether (Brij surfactant), in particular, triethyleneglycol monolauryl ether (Brij 30); sorbitan ether known as SPAN, in particular, sorbitan trioleate (Span 85) and sorbitan monolaurate. Mixtures of surface active agents such as Tween 80/Span 85 can be used. A combination of polyoxyethylene sorbitan ester such as Tween 80 and octoxynol such as Triton X-100 is also suitable. A combination of Laureth 9 and Tween and/or octoxynol is also advantageous. Preferably, the amount of polyoxyethylene sorbitan ester (such as Tween 80) included may be 0.01% to 1% (w/v), 0.01% to 0.1% (w/v), 0.01% to 0.05% (w/v), or about 0.02%; the amount of octylphenoxy polyoxyethanol or nonylphenoxy polyoxyethanol (such as Triton X-100) included may be 0.001% to 0.1% (w/v), in particular 0.005% to 0.02%; and the amount of polyoxyethylene ether (such as Laureth 9) included may be 0.1% to 20% (w/v), possibly 0.1% to 10%, in particular 0.1% to 1% or about 0.5%.

In some embodiments, the mixed carrier, 21-valent pneumococcal conjugate composition may be delivered via a release control system. For example, intravenous infusion, transdermal patch, liposome, or other routes can be used for administration. In one aspect, macromolecules such as microsphere or implant can be used.

The above disclosure generally describes the present invention. A more complete understanding can be obtained by reference to the following specific examples. These examples are described solely for the purpose of illustration and are not intended to limit the scope of the invention.

EXAMPLES

Example 1. Preparation of *S. pneumoniae* Capsular Polysaccharides

Cultivation of *S. pneumoniae* and purification of capsular polysaccharides were conducted as known to one of skill in the art. *S. pneumoniae* serotypes were obtained from the American Type Culture Collection (ATCC) (serotype 1: ATCC No. 6301; serotype 3: ATCC No. 6303; serotype 4: ATCC No. 6304; serotype 5: ATCC No. 6305; serotype 6A: ATCC No. 6306; serotype 6B: ATCC No. 6326; serotype 7F: ATCC No. 10351; serotype 9N: ATCC No. 6309; serotype 9V: ATCC No. 10368; serotype 14: ATCC No. 6314; serotype 18C: ATCC No. 10356; serotype 19A: ATCC No. 10357; serotype 19F: ATCC No. 6319; serotype 23F: ATCC No. 6323). Internal strains for serotypes 8, 10A, 11A, 12F, 15B, 22F, and 33F were used, but any publically available strain can be used. *S. pneumoniae* were characterized by capsules and motility, Gram-positive, lancet-shaped diplococcus, and alpha hemolysis in a blood agar medium. Serotypes were identified by Quelling test using specific anti-sera (U.S. Pat. No. 5,847,112).

Preparation of Cell Banks

Several generations of seed stocks were generated in order to expand the strains and remove components of animal origin (generations F1, F2, and F3). Two additional generations of seed stocks were produced. The first additional generation was cultured from an F3 vial, and the subsequent generation was cultured from a vial of the first additional generation. Seed vials were stored frozen (below −70° C.) with synthetic glycerol as a cryopreservative. For cell bank preparation, all cultures were grown in a soy-based medium. Prior to freezing, cells were concentrated by centrifugation, spent medium was removed, and cell pellets were re-suspended in a fresh medium containing a cryopreservative (such as synthetic glycerol).

Culturing and Harvesting

Cultures from the working cell bank were inoculated into seed bottles containing a soy-based medium and cultured. After the target optical density (absorbance) was reached, the seed bottle was used to inoculate a fermentor containing the soy-based medium. The culturing was terminated when an optical density value started to be maintained constant. After terminating the culturing, sodium deoxycholate was added to the culture to lyse the cells. The resulting fermentor contents were cooled, and protein precipitation was induced. Then, the mixture was centrifuged to remove precipitated proteins and cell debris.

Purification

The solution obtained from the centrifugation was filtered through a depth filter to remove the proteins and cell debris that had not precipitated in the centrifugation. The filtrate was concentrated on a 100 kDa MW membrane and the concentrate was diafiltered with 10 volumes of a 25 mM sodium phosphate buffer (pH 7.2) to obtain a sample. The sample was filtered to collect a supernatant from which polysaccharides were precipitated and filtered. The filtrate was concentrated on a 30 kDa membrane, and the concentrate was diafiltered using about 10 volumes of triple distilled water. After performing the diafiltration, the remaining solution was filtered through a 0.2 μm filter. An in-process control test was performed on the filtrate (appearance, remaining proteins, remaining nucleic acids, endotoxins, molecular weights, and the total amount of polysaccharides). The concentrate was sterile filtered and stored at −20° C.

Example 2. Preparation of Conjugate of *S. pneumoniae* Capsular Polysaccharide and Carrier Protein Polysaccharides of different serotypes were activated following different pathways and then conjugated to a carrier protein, $CRM_{197}$ or TT. Specifically, conjugates were prepared by conjugating each of the capsular polysaccharides of all serotypes, except 15B and 22F, to $CRM_{197}$ and by conjugating each of the capsular polysaccharides of the serotypes 1, 3, 5, 15B and 22F to TT. Depending on the size of the native serotype the activation process may include reduction of the size of each capsular polysaccharide to the target molecular weight, chemical activation, and buffer exchange via ultrafiltration. The conjugates were purified using ultrafiltration and finally filtered through 0.2 μm filter. The process parameters such as pH, temperature, concentration, and time were as follows.

(1) Activation Process

Step 1: Hydrolysis

Reductive amination is a known method for conjugating polymers in which an amide bond is formed between a primary amine (—$NH_2$) group of a protein and an aldehyde of a saccharide. Aldehyde groups are added to the pneumococcal capsular polysaccharide to promote conjugation to the carrier protein. A vicinal diol structure of a monosaccharide can be oxidized by sodium periodate ($NaIO_4$) to form aldehyde groups. The capsular polysaccharides from serotypes 1, 3, 4, 6A, 8, 11A, 12F, 14, 15B, 18C, 22F, and 33F were pre-treated as follows.

In the case of the serotype 1, sodium hydroxide (at a final base concentration of 0.05 M) was added to a solution of the capsular polysaccharide, and the solution was incubated at 50±2° C. The solution was then cooled to a temperature in a range of about 21° C. to about 25° C., and hydrochloric acid was added thereto to a final pH of 6.0±0.1, thereby stopping hydrolysis.

In the case of the serotype 3, 8, 11A, and 15B, hydrochloric acid (at a final acid concentration of 0.01 M) was added to a solution of the capsular polysaccharide, and the solution was incubated at 60±2° C. The solution was then cooled to a temperature in a range of about 21° C. to about 25° C., and 0.1M sodium phosphate was added thereto to a final pH of 6.0±0.1, thereby stopping hydrolysis.

In the case of the serotype 4, hydrochloric acid (at a final acid concentration of 0.1 M) was added to a solution of the capsular polysaccharide, and the solution was incubated at 45±2° C. The solution was then cooled to a temperature in a range of about 21° C. to about 25° C., and 1M sodium phosphate was added thereto to a final pH of 6.0±0.1, thereby stopping hydrolysis.

In the case of the serotype 6A, glacial acetic acid (at a final acid concentration of 0.1 M) was added to a solution of the capsular polysaccharide, and the solution was incubated at 60±2° C. The solution was then cooled to a temperature in a range of about 21° C. to about 25° C., and 1M sodium hydroxide was added thereto to a final pH of 6.0±0.1, thereby stopping hydrolysis.

In the case of the serotype 12F, hydrochloric acid (at a final acid concentration of 0.01 M) was added to a solution of the capsular polysaccharide, and the solution was incubated at 70±2° C. The solution was then cooled to a temperature in a range of about 21° C. to about 25° C., and 0.1M sodium phosphate was added thereto to a final pH of the solution of 6.0±0.1, thereby stopping hydrolysis.

In the case of the serotypes 14 and 18C, glacial acetic acid (at a final acid concentration of 0.2 M) was added to a solution of the capsular polysaccharide, and the solution was incubated at 94±2° C. The solution was then cooled to a temperature in a range of about 21° C. to about 25° C., and 1M sodium phosphate was added thereto so that a final pH of the solution was 6.0±0.1, thereby stopping hydrolysis.

In the case of the serotypes 22F and 33F, hydrochloric acid (at a final acid concentration of 0.01 M) was added to a solution of the capsular polysaccharide, and the solution was incubated at 60±2° C. The solution was then cooled to a temperature in a range of about 21° C. to about 25° C., and 0.1M sodium phosphate was added thereto to a final pH of 6.0±0.1, thereby stopping hydrolysis.

Each of the obtained capsular polysaccharides was diluted in water for injection (WFI), sodium acetate, and sodium phosphate to a final concentration between about 1.0 mg/mL and about 2.0 mg/mL.

Step 2: Periodate Reaction

The sodium periodate molar equivalent for each pneumococcal saccharide activation was determined based on repeating unit molar mass. With thorough mixing, the oxidation reaction was allowed to proceed for 16 to 20 hours at 21° C. to 25° C. for all serotypes except for 1, 7F, and 19F, for which the temperature was 10° C. or less. To help maintain consistent and stable production of conjugates, a range of degree of oxidation (Do) levels for each serotype is targeted during the conjugation process. A preferred, targeted range for the Do levels for each serotype is shown in Table 1 and Table 2.

TABLE 1

| Range of Do for all serotypes to be conjugated to $CRM_{197}$ | |
|---|---|
| Serotype | Range of Do |
| Serotype 1 | 4 to 10 |
| Serotype 3 | 2 to 8 |
| Serotype 4 | 1 to 5 |
| Serotype 6A | 5 to 15 |
| Serotype 6B | 7 to 13 |
| Serotype 7F | 2 to 8 |
| Serotype 8 | 1 to 17 |
| Serotype 9N | 5 to 10 |

TABLE 1-continued

| Range of Do for all serotypes to be conjugated to CRM$_{197}$ | |
|---|---|
| Serotype | Range of Do |
| Serotype 9V | 4 to 9 |
| Serotype 10A | 1 to 12 |
| Serotype 11A | 1 to 15 |
| Serotype 12F | 1 to 9 |
| Serotype 14 | 6 to 13 |
| Serotype 18C | 6 to 14 |
| Serotype 19A | 7 to 13 |
| Serotype 19F | 6 to 12 |
| Serotype 23F | 6 to 14 |
| Serotype 33F | 1 to 15 |

TABLE 2

| Range of Do for serotypes 1, 3, 5, 15B and 22F to be conjugated to TT | |
|---|---|
| Serotype | Range of Do |
| Serotype 1 (1-TT) | 1 to 15 |
| Serotype 3 (3-TT) | 2 to 14 |
| Serotype 5 (5-TT) | 1 to 15 |
| Serotype 15B (15B-TT) | 1 to 15 |
| Serotype 22F (22F-TT) | 1 to 20 |

Step 3: Ultrafiltration

The oxidized saccharide was concentrated and diafiltered with WFI on a 100 kDa MWCO ultrafilter (30 kDa ultrafilter for serotype 1 and 5 kDa ultrafilter for serotype 18C). Diafiltration was conducted using 0.9% sodium chloride solution for serotype 1, 0.01 M sodium acetate buffer (pH 4.5) for serotype 7F and 23F, and 0.01 M sodium phosphate buffer (pH 6.0) for serotype 19F. The permeate was discarded, and the retentate was filtered through a 0.2 μm filter.

Step 4: Lyophilization

For capsular polysaccharides of serotypes 3, 4, 5, 8, 9N, 9V, 10A, 14, and 33F that are to be conjugated to a carrier protein by using an aqueous solvent, mixed solution of polysaccharides and carrier protein was prepared without adding further sucrose, lyophilized, and then stored at −25° C.±5° C.

For capsular polysaccharides of serotypes 1 and 18C that are to be conjugated to a carrier protein by using an aqueous solvent, polysaccharides and carrier protein were independently prepared, without adding further sucrose, lyophilized, and then stored at −25° C.±5° C.

For capsular polysaccharides of serotypes 6A, 6B, 7F, 15B-TT, 19A, 19F, 22F-TT and 23F that are to be conjugated to a carrier protein by using a DMSO solvent, a predetermined amount of sucrose to reach a final sucrose concentration of 5%±3% (w/v) was added to the activated saccharides, and the samples were independently prepared, lyophilized, and then stored at −25° C.±5° C.

For capsular polysaccharide of serotype 11A, a predetermined amount of sucrose to reach a final sucrose concentration of 20%±5% (w/v) was added to the activated saccharide, and the polysaccharides and carrier protein were independently prepared, lyophilized, and then stored at −25° C.±5° C.

For capsular polysaccharide of serotype 12F, a predetermined amount of sucrose to reach a final sucrose concentration of 10%±5% (w/v) was added to the activated saccharide, and the polysaccharides and carrier protein were independently prepared, lyophilized, and then stored at −25° C.±5° C.

(2) Conjugation Process

Aqueous conjugation was conducted for serotypes 1, 3, 4, 5, 8, 9N, 9V, 10A, 14, and 18C, and DMSO conjugation was conducted for serotypes 6A, 6B, 7F, 11A, 12F, 15B-TT, 19A, 19F, 22F-TT and 23F. Each of the capsular polysaccharides was conjugated to a carrier protein at a ratio of 0.2 to 2:1.

Step 1: Dissolution

Aqueous Conjugation

For serotypes 1, 3, 4, 5, 8, 9N, 9V, 10A, 14, 18C, and 33F, the lyophilized sample was thawed and equilibrated at room temperature. The lyophilized sample was reconstituted to a reaction concentration by using a sodium phosphate buffer solution at 23±2° C. at a ratio set for each serotype.

Dimethyl sulfoxide (DMSO) Conjugation

For serotypes 6A, 6B, 7F, 11A, 12F, 15B-TT, 19A, 19F, 22F-TT, and 23F, the lyophilized sample was thawed, equilibrated at room temperature, and reconstituted in DMSO.

Step 2: Conjugation Reaction

Aqueous Conjugation

For serotypes 3-TT, 4, 5-TT, 8, 9N, 9V, 10A, 14, 18C, and 33F, the conjugation reaction was initiated by adding the sodium cyanoborohydride solution (100 mg/mL) to 1.0 to 1.4 moles sodium cyanoborohydride per mole of saccharide. However, for serotypes 1, 1-TT and 3, the reaction was initiated by adding the sodium cyanoborohydride solution to 0.5 moles sodium cyanoborohydride per mole of saccharide.

The reaction mixture was incubated at 23° C. to 37° C. for 44 to 106 hours. The reaction temperature and time were adjusted by serotype. The temperature was then reduced to 23±2° C. and sodium chloride 0.9% was added to the reactor. Sodium borohydride solution (100 mg/mL) was added to achieve 1.8 to 2.2 molar equivalents of sodium borohydride per mole of saccharide. The mixture was incubated at 23±2° C. for 3 to 6 hours. This procedure reduced any unreacted aldehydes present on the saccharides. Then, the mixture was diluted with sodium chloride 0.9% and the diluted conjugation mixture was filtered using a 0.8 or 0.45 μm pre-filter.

DMSO Conjugation

For capsular polysaccharides of serotypes 6A, 6B, 7F, 11A, 12F, 15B-TT, 19A, 19F, 22F-TT and 23F, the conjugation reaction was initiated by adding the sodium cyanoborohydride solution (100 mg/mL) to a ratio of 0.8 to 1.2 molar equivalents of sodium cyanoborohydride per one mole of activated saccharide. WFI was added to the reaction mixture to a target concentration of 1% (v/v), and the mixture was incubated for 12 to 26 hours at 23±2° C. 100 mg/mL of a sodium borohydride solution (typical 1.8 to 2.2 molar equivalents sodium borohydride per mole activated saccharide) and WFI (target 5% v/v) were added to the reaction and the mixture was incubated for 3 to 6 hours at 23±2° C. This procedure reduced any unreacted aldehydes present on the saccharides. Then, the reaction mixture was diluted with sodium chloride 0.9%, and the diluted conjugation mixture was filtered using a 0.8 or 0.45 μm pre-filter.

Step 3: Ultrafiltration

The diluted conjugate mixture was concentrated and diafiltered on a 100 kDa MWCO ultrafiltration filter or a 300 kDa MWCO ultrafiltration filter with a minimum of 15 volumes of 0.9% sodium chloride or buffer. Also, the composition and pH of the buffer used in the process varied depending on each of the serotypes.

Step 4: Sterile Filtration

The retentate after the ultrafiltration was sterile filtered (0.2 μm), and in-process controls (appearance, free protein, free saccharide, molecular size distribution, sterility, saccharide content, protein content, pH, endotoxin, residual cyanide, residual DMSO, saccharide identity, TT identity, and $CRM_{197}$ identity) were performed on the filtered conjugates. The final concentrate was refrigerated and stored at 2° C. to 8° C.

Example 3. Formulation of Multivalent Pneumococcal Conjugate Vaccine

The desired volumes of final bulk concentrates obtained from Example 2 were calculated based on the batch volume and the bulk saccharide concentrations. After the 0.85% sodium chloride (physiological saline), polysorbate 80, and succinate buffer were added to the pre-labeled formulation vessel, bulk concentrates were added. The preparation was then thoroughly mixed and sterile filtered through a 0.2 μm membrane. The formulated bulk was mixed gently during and following the addition of bulk aluminum phosphate. The pH was checked and adjusted if necessary. The formulated bulk product was stored at 2 to 8° C. The following, non-limiting, multivalent pneumococcal conjugate vaccine formulations were prepared and named PCV21(1/5/15B/22F)-TT and PCV21(3/5/15B/22F)-TT:

PCV21(1/5/15B/22F)-TT included polysaccharide-conjugates prepared by conjugating each polysaccharide of the serotypes 1, 5, 15B and 22F to TT and each polysaccharide of the serotypes 3, 4, 6A, 6B, 7F, 8, 9N, 9V, 10A, 11A, 12F, 14, 18C, 19A, 19F, 23F, and 33F to $CRM_{197}$; and PCV21(3/5/15B/22F)-TT included polysaccharide-conjugates prepared by conjugating each polysaccharide of the serotypes 3, 5, 15B and 22F to TT and each polysaccharide of the serotypes 1, 4, 6A, 6B, 7F, 8, 9N, 9V, 10A, 11A, 12F, 14, 18C, 19A, 19F, 23F, and 33F to $CRM_{197}$.

The PCV21(1/5/15B/22F)-TT composition in a total dose of 0.5 ml included 2.2 μg of each polysaccharide, except for serotype 6B at 4.4 μg; 2 μg to 25 μg of TT (for serotypes 1, 5, 15B, and 22F) and 40 μg to 75 μg $CRM_{197}$, 0.125 mg of elemental aluminum (0.5 mg aluminum phosphate) adjuvant; 4.25 mg of sodium chloride; about 295 μg of a succinate buffer solution; and about 100 μg of polysorbate 80 in the total of 0.5 ml dose.

The PCV21(3/5/15B/22F)-TT composition in a total dose of 0.5 ml included 2.2 μg of each polysaccharide, except for serotypes 1, 3, 6B, 19A, and 19F at 4.4 μg; 2 μg to 25 μg of TT (for serotypes 3, 5, 15B, and 22F), 0.250 mg of elemental aluminum (1.13 mg aluminum phosphate), with the other components and contents thereof identical to those of PCV21(1/5/15B/22F)-TT.

Example 4. Immunogenicity of Multivalent Pneumococcal Conjugate Vaccine

The mixed carrier, multivalent pneumococcal vaccines, PCV21(1/5/15B/22F)-TT and PCV21(3/5/15B/22F)-TT prepared in Example 3, were tested for the ability to induce an immunogenic response in rabbits. Immunogenicity assessment was performed by antigen-specific ELISA for serum IgG concentrations and by opsonophagocytic assay (OPA) for antibody functionality. New Zealand White rabbits were immunized intramuscularly at week 0 and week 2 with a dose of 5% higher than the planned human clinical dose of each polysaccharide (2.31 μg of each polysaccharide, except for 6B at 4.62 μg) in the formulation or the human dose (2.2 ug of each polysaccharide, except for 6B at 4.4 ug). Sera were sampled every 2 weeks post immunization. Both concentrations showed the same results.

4-1. PCV21(3/5/15B/22F)-TT

Serotype Specific IgG Concentration Measurement

Capsular polysaccharides (PnPs) for each serotype were coated on a 96-well plate at 0.5 μg/well to 1 μg/well. An equivalent amount of serum was sampled from each subject and was pooled by group. The serum pool was serially diluted by 2.5 times with an antibody dilution buffer comprising Tween 20 and pneumococcal cell-wall polysaccharide (CWPS) obtained from Statens Serum Institut (5 μg/mL) and then reacted at room temperature for 30 minutes. The plate was washed 5 times with a washing buffer and then pre-adsorbed and diluted serum 50 μl was added to the coated well plate, followed by incubation at room temperature for 2 hours to 18 hours. The well plate was washed in the same way and then goat anti-Rabbit IgG-alkaline phosphatase conjugates were added to each well, followed by incubation at room temperature for 2 hours. Plates were washed as described above and 1 mg/mL p-nitrophenylamine buffer as substrate was added to each well and then reacted at room temperature for 2 hours. The reaction was quenched by adding 50 μl of 3 M NaOH and absorbances at 405 nm and 690 nm were measured. As a comparative example, the commercially available, 13-valent vaccine (PREVNAR13) was subjected to the same procedure. The results are shown in Table 3.

TABLE 3

| IgG concentration (U/mL) for 21 serotypes at 2 weeks after secondary immunization | | |
|---|---|---|
| Serotype | PREVNAR13 | PCV21(3/5/15B/22F)-TT |
| 1 | 16770.4 | 13623.9 |
| 3 | 6603.4 | 29462.4 |
| 4 | 27969.9 | 44594.4 |
| 5 | 5758.6 | 10521.4 |
| 6A | 9493.7 | 12696.6 |
| 6B | 8690.6 | 8197.1 |
| 7F | 60819.7 | 56995.0 |
| 8 | 594.8 | 61898.5 |
| 9N | 5186.2 | 293936.9 |
| 9V | 30043.9 | 39421.1 |
| 10A | 169.8 | 27243.3 |
| 11A | 184.5 | 52384.3 |
| 12F | 130.0 | 26815.4 |
| 14 | 21906.0 | 39258.8 |
| 15B | 843.5 | 8360.7 |
| 18C | 91500.7 | 80523.0 |
| 19A | 16470.7 | 5179.7 |
| 19F | 13956.4 | 17673.4 |
| 22F | 139.7 | 11716.5 |
| 23F | 12089.4 | 8934.6 |
| 33F | 143.2 | 29774.3 |

When the capsular polysaccharides of serotypes 3 and 5 were conjugated to TT, the serotype specific IgG concentration significantly increased compared to that obtained when they were conjugated to $CRM_{197}$. Rabbits immunized with PCV21(3/5/15B/22F)-TT also demonstrated significant increases in IgG concentration against the additional eight serotypes not present in PREVNAR13 (i.e., 8, 9N, 10A, 11A, 12F, 15B, 22F, and 33F). Serotype 9N, in particular, had a greater than 50-fold increase in serum specific IgG concentration relative to PREVNAR13.

Functional Immunogenicity Test (MOPA)

Antibody functions were evaluated by testing serum in a MOPA assay. *S. pneumoniae* MOPA strain stored at −70° C. or lower was diluted to the corresponding final dilution fold so that a concentration of each strain was about 50,000

CFU/mL. An equivalent amount of serum was sampled from each subject, pooled by group and 2-fold serially diluted so that 20 µl of serum remained in a U-bottom plate. After diluting the sample, 10 µl of the strain prepared for each serotype was mixed with the diluted sample, and the mixture was allowed to react at room temperature for 30 minutes so that *S. pneumoniae* and the antibody were well mixed. A mixture of pre-differentiated HL-60 cells and complement was added and reacted in a $CO_2$ incubator (37° C.) for 45 minutes. The temperature was reduced to stop phagocytosis and 10 µl of the reaction solution was spotted onto an agar plate pre-dried for 30 to 60 minutes, and then allowed to be absorbed onto the plate for 20 minutes until drying. A 25 mg/mL TTC stock solution was added to a prepared overlay agar, and an antibody appropriate for the corresponding strain was added thereto. The mixture was thoroughly mixed, and then about 25 mL of the mixture was added onto the plate and hardened for about 30 minutes. The completely hardened plate was incubated in a $CO_2$ incubator (37° C.) for 12 to 18 hours and then colonies were counted. MOPA titer was expressed as a dilution rate at which 50% killings were observed. As a comparative example, the commercially-available, 13-valent vaccine (PREVNAR13) was subjected to the same procedure. The results are shown in Tables 4.

TABLE 4

MOPA titers for 21 serotypes at 2 weeks after secondary immunization

| Serotype | PREVNAR13 | PCV21(3/5/15B/22F)-TT |
|---|---|---|
| 1 | 94 | 80 |
| 3 | 829 | 3772 |
| 4 | 2428 | 2370 |
| 5 | 1169 | 1972 |
| 6A | 4925 | 3094 |
| 6B | 5693 | 3927 |
| 7F | 2731 | 2386 |
| 8 | Not tested | 669 |
| 9N | Not tested | 2339 |
| 9V | 271 | 175 |
| 10A | Not tested | 805 |
| 11A | Not tested | 2040 |
| 12F | Not tested | 894 |
| 14 | 1917 | 1874 |
| 15B | Not tested | 311 |
| 18C | 5347 | 3758 |
| 19A | 5760 | 888 |
| 19F | 2059 | 710 |
| 22F | Not tested | 1286 |
| 23F | 1975 | 1868 |
| 33F | Not tested | 1011 |

When the serotypes 3 and 5 were conjugated to TT, functional MOPA titers significantly increased compared to MOPA titers obtained when they were conjugated to $CRM_{197}$. Rabbits immunized with PCV21(3/5/15B/22F)-TT also demonstrated significant increases in functional MOPA titers against each of the additional eight serotypes that are not present in PREVNAR13 (i.e., 8, 9N, 10A, 11A, 12F, 15B, 22F, and 33F).

4-2. PCV21(1/5/15B/22F)-TT

The serotype specific IgG concentration and functional immunogenicity titer were measured in the same manner as in 4-1, and the results of two separate experiments are shown as follows.

Serotype Specific IgG Concentration Measurement

TABLE 5

IgG concentration (U/mL) for 21 serotypes at 2 weeks after secondary immunization

| | Experiment 1 | | Experiment 2 | |
|---|---|---|---|---|
| Serotype | PREVNAR13 | PCV21(1/5/15B/22F)-TT | PREVNAR13 | PCV21(1/5/15B/22F)-TT |
| 1 | 5105.5 | 46202.4 | 14208.3 | 28405.2 |
| 3 | 6303.0 | 10591.0 | 6575.6 | 8883.8 |
| 4 | 46727.3 | 69813.7 | 16600.3 | 39330.1 |
| 5 | 6873.9 | 16468.4 | 5079.3 | 21510.8 |
| 6A | 32561.4 | 34321.1 | 8965.5 | 7658.8 |
| 6B | 25398.7 | 20484.6 | 5105.2 | 2885.6 |
| 7F | 27560.5 | 85909.1 | 59993.0 | 55489.8 |
| 8 | 521.0 | 89658.7 | 274.7 | 83945.4 |
| 9N | 5198.2 | 304294.1 | 3824.7 | 207073.2 |
| 9V | 62169.3 | 41229.0 | 39503.5 | 42000.7 |
| 10A | 166.4 | 37705.0 | 130.0 | 19173.7 |
| 11A | 195.3 | 43766.3 | 163.9 | 49047.9 |
| 12F | 154.4 | 25797.6 | 130.0 | 14503.3 |
| 14 | 17765.9 | 34321.5 | 12312.4 | 18367.4 |
| 15B | 436.0 | 4658.6 | 280.6 | 6711.2 |
| 18C | 103154.7 | 158798.8 | 62963.5 | 95617.7 |
| 19A | 19191.1 | 6398.0 | 9807.5 | 4133.7 |
| 19F | 16349.2 | 37946.5 | 9838.7 | 12775.0 |
| 22F | 130.0 | 10335.4 | 130.0 | 1705.8 |
| 23F | 15166.5 | 10104.6 | 5835.1 | 4128.6 |
| 33F | 146.1 | 35918.2 | 141.4 | 34004.5 |

When the capsular polysaccharides of serotypes 1 and 5 were conjugated to TT, the serotype specific IgG concentration significantly increased compared to that obtained when they were conjugated to $CRM_{197}$. Rabbits immunized with PCV21(1/5/15B/22F)-TT also demonstrated significant increases in IgG concentration against the additional eight serotypes not present in PREVNAR13 (i.e., 8, 9N, 10A, 11A, 12F, 15B, 22F, and 33F). Again, serotype 9N showed a significant increase (greater than 50-fold) relative to PRE-NAR13.

Functional Immunogenicity Test (MOPA)

TABLE 6

MOPA titers for 21 serotypes at 2 weeks after secondary immunization

| | Experiment 1 | | Experiment 2 | |
|---|---|---|---|---|
| Serotype | PREVNAR13 | PCV21(1/5/15B/22F)-TT | PREVNAR13 | PCV21(1/5/15B/22F)-TT |
| 1 | 99 | 294 | 109 | 214 |
| 3 | 479 | 792 | 740 | 820 |
| 4 | 2560 | 4083 | 2272 | 2671 |
| 5 | 1046 | 2696 | 3638 | 13927 |
| 6A | 5624 | 4871 | 4949 | 2417 |
| 6B | 5451 | 9599 | 4915 | 4516 |
| 7F | 2355 | 2585 | 2414 | 2305 |
| 8 | Not tested | 692 | — | 779 |
| 9N | 54 | 1860 | 84 | 1391 |
| 9V | 282 | 165 | 295 | 371 |
| 10A | Not tested | 949 | — | 810 |
| 11A | Not tested | 986 | — | 2118 |
| 12F | Not tested | 795 | — | 713 |
| 14 | 1052 | 2715 | 1659 | 2362 |
| 15B | 59 | 461 | 79 | 403 |
| 18C | 6257 | 7200 | 2933 | 3261 |
| 19A | 2962 | 1151 | 3910 | 1794 |
| 19F | 968 | 1874 | 1570 | 1109 |
| 22F | Not tested | 2091 | — | 261 |
| 23F | 1854 | 1481 | 1956 | 660 |
| 33F | Not tested | 1862 | — | 850 |

When the serotypes 1 and 5 were conjugated to TT, functional MOPA titers significantly increased compared to MOPA titers obtained when they were conjugated to $CRM_{197}$. Rabbits immunized with PCV21(3/5/15B/22F)-TT also demonstrated significant increases in functional MOPA titers against each of the additional eight serotypes that are not present in PREVNAR13 (i.e., 8, 9N, 10A, 11A, 12F, 15B, 22F, and 33F).

Example 5. Additional Details about Preparation of Saccharide-Protein Conjugate from *Streptococcus pneumoniae* Serotype 9N Preparation of Cell Bank

*Streptococcus pneumoniae* serotype 9N (ATCC 6309) was acquired from the American Type Culture Collection (ATCC). For proliferation of the strain and removal of constituents of animal origin, the seed stock was cultured for several generations. The stock vial was kept in a refrigerator (<−70° C.) together with synthetic glycerol as a cryoprotectant. For preparation of a cell bank, the cell culture was proliferated in a soy-based medium. Prior to freezing, the cells were concentrated by centrifugation and, after removing the medium used, the cell pellets were resuspended in a fresh medium containing a cryoprotectant (e.g., synthetic glycerol).

Fermentation

The culture from the cell bank was inoculated into a seed bottle containing a soy-based medium. Until the growth condition was satisfied, the culture was incubated at constant temperature without agitation. The culture was inoculated into a seed fermenter containing a soy-based medium, with temperature, pH and agitation speed controlled, using a seed bottle. Fermentation was terminated after the growth was stopped or the working capacity of the fermenter was reached. After terminating the fermentation by adding a deactivator, cell debris were removed using a combination of continuous flow centrifugation and filtration.

Purification

The pneumococcal polysaccharide purification process consisted of multilayer filtration, repeated concentration/diafiltration and filtration/elution.

Activation

The final polysaccharide concentration was adjusted to about 2.0 g/L by sequentially adding WFI of a calculated amount. If necessary, the reaction pH was adjusted to approximately 6.0. After the pH adjustment, the reaction temperature was adjusted to 21-25° C. Approximately 0.024-0.189 mg of sodium periodate was added per 1 mg of sugar to initiate oxidation. The oxidation reaction was conducted for 16-20 hours at 21-25° C.

The activated polysaccharide was concentrated and diafiltered using a 100-kDa MWCO ultrafiltration membrane. The diafiltration was conducted for WFI of 10 times the volume of the diafiltration volume. Then, the purified activated polysaccharide was stored at 2-8° C. The purified activated saccharide was characterized by (i) the saccharide concentration determined by colorimetric assay, (ii) the aldehyde concentration determined by colorimetric assay, (iii) the degree of oxidation and (iv) the molecular weight measured by SEC-MALLS.

SEC-MALLS is used to determine the molecular weight of polysaccharides and polysaccharide-protein conjugates. SEC is used to separate the polysaccharide based on the hydrodynamic volume. A refractive index (RI) detector and a multi-angle laser light scattering (MALLS) detector are used to determine the molecular weight. When light reacts with a material, the light is scattered. The quantity of the scattered light is related with the concentration, the square of dn/dc (specific refractive index increment) and the molar mass of the material. The molecular weight is calculated based on the signal of the scattered light from the MALLS detector and the concentration signal from the RI detector.

The degree of oxidation (DO) of the activated polysaccharide is determined as the mole of sugar repeat units divided by the mole of aldehyde. The mole of sugar repeat units is determined by various colorimetric techniques, e.g., using anthrone assay. And, the mole of aldehyde is determined by the Park-Johnson colorimetric assay.

Using these techniques described above, it was determined that the activated *Streptococcus pneumoniae* serotype 9N capsular polysaccharide obtained by the method described above has a degree of oxidation of 2-19, more typically 5-10, and a molecular weight of about 200-700 kDa.

Conjugation

The activated polysaccharide was blended with the carrier protein $CRM_{197}$, at a ratio of 0.5-2 g of $CRM_{197}$ per 1 g of the activated polysaccharide. Then, the blended mixture was lyophilized. The lyophilized mixture of the activated polysaccharide and $CRM_{197}$ was stored at −20° C.

The lyophilized mixture of the activated polysaccharide and $CRM_{197}$ was reconstituted in a 0.1 M sodium phosphate solution and then mixed sufficiently. The final polysaccharide concentration in the reaction solution was about 10-20 g/L. After initiating conjugation by adding 1.0-1.2 molar equivalents of sodium cyanoborohydride ($NaBH_3CN$) to the reaction mixture, the reaction was conducted at 35-39° C. for 44-52 hours. The conjugation reaction was terminated by adding a 0.9% sodium chloride solution of the same volume as the conjugation reaction solution and then adding 1.8-2.2 molar equivalents of sodium borohydride ($NaBH_4$) to cap the unreacted aldehyde. The capping reaction was conducted at 21-25° C. for 3-6 hours.

The conjugate solution was diluted with a 0.9% sodium chloride solution for concentration and diafiltration using a 100-kDa MWCO membrane. The diluted conjugate solution was filtered through a 0.8-0.45 m filter and purified by concentration and diafiltration.

The diafiltration using a 100-kDa MWCO membrane was conducted using a 0.9% sodium chloride solution of 15-40 times the diafiltration volume. After the diafiltration was completed, the remaining solution was filtered through a 0.2 m filter. The conjugate solution was diluted to a concentration below approximately 0.55 mg/mL, sterile-filtered and then stored at 2-8° C.

The purified serotype 9N conjugate was characterized, in particular, by (i) the protein concentration determined by colorimetric (Lowry) assay, (ii) the aldehyde concentration determined by colorimetric assay, (iii) the saccharide-to-protein ratio, (iv) the molecular size distribution determined by size exclusion chromatography (CL-4B) and (v) the molecular weight measured by SEC-MALLS.

The change in the characteristics of the serotype 9N conjugate was observed while varying the degree of oxidation (DO). The result is summarized in Table 7.

TABLE 7

| | Conjugate number | | | | | |
|---|---|---|---|---|---|---|
| | 1 | 2 | 3 | 4 | 5 | 6 |
| Molecular weight of activated polysaccharide, kDa | 582 | 619 | 459 | 563 | 490 | 427 |
| DO | 18.2 | 9.4 | 7.4 | 6.7 | 4.3 | 2.3 |
| Input ratio (P:S) | | | 0.8:1 | | | |
| Polysaccharide concentration in conjugation reaction solution, g/L | | | 20.0 | | | |
| % conjugate yield | 53 | 43 | 39 | 32 | 33 | 39 |
| Saccharide-to-protein ratio | 2.1 | 1.5 | 1.3 | 1.1 | 1.0 | 0.78 |
| % free saccharide | 44 | 28 | 22 | 20 | 21 | 31 |
| % molecular weight distribution | 52 | 49 | 50 | 55 | 44 | 31 |
| Molecular weight of conjugate, kDa | 860 | 1,110 | 1,912 | 1,168 | 1,189 | 1,160 |

The change in the characteristics of the serotype 9N conjugate was observed while varying the blending ratio of the activated polysaccharide and $CRM_{197}$ during the lyophilization. The result is summarized in Table 8.

TABLE 8

| | Conjugate number | | | | |
|---|---|---|---|---|---|
| | 7 | 8 | 9 | 10 | 11 |
| Molecular weight of activated polysaccharide, kDa | | | 287 | | |
| DO | | | 5.6 | | |
| Input ratio (P:S) | 2:1 | 1.5:1 | 1:1 | 0.67:1 | 0.5:1 |
| Polysaccharide concentration in conjugation reaction solution, g/L | | | 20.0 | | |
| % conjugate yield | 25 | 50 | 43 | 41 | 66 |
| Saccharide-to-protein ratio | 0.71 | 0.85 | 1.0 | 1.2 | 1.8 |
| % free saccharide | 5 | 6 | 15 | 27 | 62 |
| % molecular weight distribution | 52 | 58 | 50 | 40 | 22 |
| Molecular weight of conjugate, kDa | 3,720 | 3,713 | 1,327 | 1,016 | 545 |

The change in the characteristics of the serotype 9N conjugate was observed while varying the polysaccharide concentration in the conjugation reaction solution. The result is summarized in Table 9.

TABLE 9

| | Conjugate number | | | | |
|---|---|---|---|---|---|
| | 12 | 13 | 14 | 15 | 16 |
| Molecular weight of activated polysaccharide, kDa | | | 560 | | |
| DO | | | 6.1 | | |
| Input ratio (P:S) | | | 0.8:1 | | |
| Polysaccharide concentration in conjugation reaction solution, g/L | 10.0 | 12.5 | 15.0 | 17.5 | 20.0 |
| % conjugate yield | 20 | 31 | 28 | 40 | 42 |
| Saccharide-to-protein ratio | 1.0 | 1.0 | 0.93 | 0.99 | 0.97 |
| % free saccharide | 32 | 30 | 22 | 21 | 18 |
| % molecular weight distribution | 17 | 27 | 40 | 47 | 54 |
| Molecular weight of conjugate, kDa | 560 | 546 | 845 | 932 | 1,438 |

Example 6. Analysis of Immunogenicity

A monovalent conjugate composition containing the *Streptococcus pneumoniae* serotype 9N saccharide-protein conjugate conjugated to $CRM_{197}$ was formulated.

The immunogenicity of the monovalent immunogenic compositions of Tables 11-13 was analyzed by ELISA. The serum concentration of the serotype-specific IgG was determined.

Five female New Zealand white rabbits weighing 2.5-3.5 kg were immunized with the proposed human clinical dose (conjugate 2.2 µg; +0.25 mg/mL aluminum as $AlPO_4$) at 0 week via an intramuscular route. The rabbits were immunized again at week 2 with the conjugate vaccine of the same dose and blood samples were taken at week 4. Serotype-specific ELISA was conducted for serum samples at week 0 and week 4.

The analysis result is shown in Table 10. The rabbits immunized with the monovalent conjugate composition (conjugate number 8) showed significant increase in the total IgG titer for the serotype 9N. The rabbits immunized with other conjugates also showed significant increase in the total IgG titer.

Table 10 shows a result of measuring the IgG concentration after immunizing the rabbits with the conjugate number 8 of Table 8.

TABLE 10

| | IgG concentration (U/mL) | |
|---|---|---|
| Serotype | Pre-immunization | Post-immunization |
| 9N | 130.0 | 656,345.3 |

While one or more exemplary embodiments have been described in the specification, it will be understood by those of ordinary skill in the art that various changes in form and details may be made therein without departing from the spirit and scope of the inventive concept as defined by the following claims.

REFERENCES

The following references are cited in the application and provide general information regarding the technical field and provide assays and other details discussed in the application.

The following references are incorporated herein by reference in their entirety.

[1] Prymula et al., *The Lancet*, 367:740-48 (2006).
[2] Vesikari et al., *PIDJ*, 28(4):S66-76 (2009).
[3] Dagan et al., *Infection & Immunity*, 5383-91 (2004).
[4] Juergens et al., *Clinical and Vaccine Immunology*, 21(9): 1277-1281 (2014).
[5] Andrews et al., *The Lancet*, 14:839-846 (2014).
[6] Nurkka et al., *Vaccine*, 20:194-201 (2001).
[7] Levin and Stone, *J. Immunol.*, 67:235-242 (1951).
[8] W.H.O. Manual for the Production and Control of Vaccines: Tetanus Toxoid, 1977 (BLG/UNDP/77.2 Rev.I.)
[9] Didierlaurent et al., *J. Immunol.*, 183:6186-6197 (2009).

What is claimed is:

1. A monovalent pneumococcal conjugate composition comprising a serotype 9N conjugate, wherein the serotype 9N conjugate comprises a protein carrier conjugated to a capsular polysaccharide from *Streptococcus pneumoniae* serotype 9N, wherein the protein carrier is $CRM_{197}$, wherein the capsular polysaccharide from serotype 9N is conjugated to $CRM_{197}$ in a state where the capsular polysaccharide from serotype 9N is activated to have a degree of oxidation of 2-19 and a molecular weight of 200-700 kDa, and wherein the monovalent pneumococcal conjugate composition comprises less than 45% of a free capsular polysaccharide from serotype 9N based on the total amount of the capsular polysaccharide from serotype 9N.

2. The monovalent pneumococcal conjugate composition of claim 1, wherein the capsular polysaccharide from serotype 9N is conjugated to $CRM_{197}$ in a state where the capsular polysaccharide from serotype 9N is activated to have a degree of oxidation of 5-10.

3. The monovalent pneumococcal conjugate composition of claim 1, wherein the monovalent pneumococcal conjugate composition comprises less than 40% of a free capsular polysaccharide from serotype 9N based on the total amount of the capsular polysaccharide from serotype 9N.

4. The monovalent pneumococcal conjugate composition of claim 1, wherein the serotype 9N conjugate has a molecular weight of 500-4,000 kDa.

5. The monovalent pneumococcal conjugate composition of claim 1, wherein the ratio of the capsular polysaccharide from serotype 9N to $CRM_{197}$ in the serotype 9N conjugate is 0.1-5 (w/w).

6. The monovalent pneumococcal conjugate composition of claim 5, wherein the ratio of the capsular polysaccharide from serotype 9N to $CRM_{197}$ in the serotype 9N conjugate is 0.5-2.5 (w/w).

7. The monovalent pneumococcal conjugate composition of claim 1, wherein 15-60% of the serotype 9N conjugate has a $K_d$ of 0.3 or below as measured in a CL-4B column.

8. The monovalent pneumococcal conjugate composition of claim 1, wherein the capsular polysaccharide from serotype 9N is conjugated with the $CRM_{197}$ by adding 0.02-0.19 μg of periodate per 1 μg of sugar, and wherein the serotype 9N conjugate has a molecular weight of 500-4,000 kDa, a molecular weight distribution of 15-60% with a $K_d$ of 0.3 or below as measured in a CL-4B column, and a saccharide/protein ratio of 0.5-2.5.

9. The monovalent pneumococcal conjugate composition of claim 1, further comprising an adjuvant.

10. The monovalent pneumococcal conjugate composition of claim 9, wherein the adjuvant is an aluminum-based adjuvant.

11. The monovalent pneumococcal conjugate composition of claim 10, wherein the adjuvant is selected from the group consisting of aluminum phosphate, aluminum sulfate, and aluminum hydroxide.

12. The monovalent pneumococcal conjugate composition of claim 11, wherein the adjuvant is aluminum phosphate.

13. A vaccine comprising the monovalent pneumococcal conjugate composition of claim 1 and a pharmaceutically acceptable excipient.

14. The vaccine of claim 13, wherein the vaccine is formulated as a single 0.5 ml dose comprising 2 μg to 2.5 μg of the capsular polysaccharide from serotype 9N.

15. The vaccine of claim 14, wherein the vaccine is formulated as a single 0.5 ml dose comprising 2.2 μg of the capsular polysaccharide from serotype 9N.

* * * * *